(12) United States Patent
Freeman et al.

(10) Patent No.: US 12,094,595 B2
(45) Date of Patent: Sep. 17, 2024

(54) AR/XR HEADSET FOR MILITARY MEDICAL TELEMEDICINE AND TARGET ACQUISITION

(71) Applicant: Raytrx, LLC, Tulsa, OK (US)

(72) Inventors: Michael Hayes Freeman, Tulsa, OK (US); Mitchael C. Freeman, Sapulpa, OK (US); Jordan Boss, Tulsa, OK (US)

(73) Assignee: RAYTRX, LLC, Tulsa, OK (US)

( * ) Notice: Subject to any disclaimer, the term of this patent is extended or adjusted under 35 U.S.C. 154(b) by 376 days.

(21) Appl. No.: 17/307,984

(22) Filed: May 4, 2021

(65) Prior Publication Data

US 2021/0257084 A1 Aug. 19, 2021

Related U.S. Application Data

(63) Continuation-in-part of application No. 15/073,144, filed on Mar. 17, 2016, now Pat. No. 9,955,862, and
(Continued)

(51) Int. Cl.
*G16H 30/40* (2018.01)
*A61B 3/00* (2006.01)
(Continued)

(52) U.S. Cl.
CPC ........... *G16H 30/40* (2018.01); *A61B 3/0025* (2013.01); *A61B 3/024* (2013.01); *A61B 3/032* (2013.01);
(Continued)

(58) Field of Classification Search
CPC ........ G16H 30/40; G16H 30/20; G16H 10/60; G16H 50/20; G16Z 99/00; A61B 3/0025;
(Continued)

(56) References Cited

U.S. PATENT DOCUMENTS 8,579,194 B2 11/2013 Boss et al.
9,651,786 B1 * 5/2017 Browne ................. G02B 26/04
(Continued)

FOREIGN PATENT DOCUMENTS

EP 4052647 9/2022
JP 5571901 B2 8/2014
(Continued)

OTHER PUBLICATIONS

KIPO, "International Search Report", Aug. 23, 2021, Published in: WO.
(Continued)

*Primary Examiner* — Mark Edwards
(74) *Attorney, Agent, or Firm* — Howard & Howard Attorneys PLLC

(57) ABSTRACT

An AXR headset may be used for remote telemedicine applications on the battlefield to assist generalist medical care providers on the battlefield or battlefield surgical care facility with specialist care providers though shared visualization, conversation, and data. In addition, the AXR headset for warfighters permits better target acquisition and visualization system comprising an AXR headset and a digital sight capable of being mounted on a weapon, the digital sight in communication with the AXR headset. The digital sight may be an existing weapon sight with an additional digital camera added, or the digital sight may be a sighting module of a digital nature capable of sending target information to the AXR headset.

13 Claims, 12 Drawing Sheets

Related U.S. Application Data a continuation-in-part of application No. 15/940,561, filed on Mar. 29, 2018, now Pat. No. 10,111,583, which is a continuation of application No. 15/073,144, filed on Mar. 17, 2016, now Pat. No. 9,955,862, application No. 17/307,984, filed on May 4, 2021 is a continuation-in-part of application No. 16/173,719, filed on Oct. 29, 2018, now Pat. No. 10,874,297, which is a continuation of application No. 15/940,561, filed on Mar. 29, 2018, now Pat. No. 10,111,583, application No. 17/307,984, filed on May 4, 2021 is a continuation-in-part of application No. 17/137,069, filed on Dec. 29, 2020, which is a continuation of application No. 16/173,719, filed on Oct. 29, 2018, now Pat. No. 10,874,297, application No. 17/307,984, filed on May 4, 2021 is a continuation-in-part of application No. 17/137,093, filed on Dec. 29, 2020, which is a continuation-in-part of application No. 16/173,719, filed on Oct. 29, 2018, now Pat. No. 10,874,297, application No. 17/307,984, filed on May 4, 2021 is a continuation-in-part of application No. 17/151,174, filed on Jan. 17, 2021, now Pat. No. 11,031,120, which is a continuation of application No. 17/137,093, filed on Dec. 29, 2020, application No. 17/307,984, filed on May 4, 2021 is a continuation-in-part of application No. 15/962,661, filed on Apr. 25, 2018, now Pat. No. 11,956,414, which is a continuation-in-part of application No. 15/073,144, filed on Mar. 17, 2016, now Pat. No. 9,955,862, application No. 17/307,984, filed on May 4, 2021 is a continuation-in-part of application No. 16/511,202, filed on Jul. 15, 2019, now Pat. No. 11,461,936, which is a continuation-in-part of application No. 15/073,144, filed on Mar. 17, 2016, now Pat. No. 9,955,862, and a continuation-in-part of application No. 15/940,561, filed on Mar. 29, 2018, now Pat. No. 10,111,583, and a continuation-in-part of application No. 16/173,719, filed on Oct. 29, 2018, now Pat. No. 10,874,297, and a continuation-in-part of application No. 15/962,661, filed on Apr. 25, 2018, now Pat. No. 11,956,414, application No. 17/307,984, filed on May 4, 2021 is a continuation-in-part of application No. 16/511,451, filed on Jul. 15, 2019, now Pat. No. 11,016,302, which is a continuation-in-part of application No. 16/511,202, filed on Jul. 15, 2019, now Pat. No. 11,461,936, application No. 17/307,984, filed on May 4, 2021 is a continuation-in-part of application No. 17/034,944, filed on Sep. 28, 2020, now Pat. No. 11,819,273, which is a continuation-in-part of application No. 16/173,719, filed on Oct. 29, 2018, now Pat. No. 10,874,297, and a continuation-in-part of application No. 15/962,661, filed on Apr. 25, 2018, now Pat. No. 11,956,414, and a continuation-in-part of application No. 16/511,451, filed on Jul. 15, 2019, now Pat. No. 11,016,302, application No. 17/307,984, filed on May 4, 2021 is a continuation-in-part of application No. 17/182,022, filed on Feb. 22, 2021, now Pat. No. 11,628,038.

(60) Provisional application No. 63/019,796, filed on May 4, 2020, provisional application No. 62/134,422, filed on Mar. 17, 2015, provisional application No. 62/489,801, filed on Apr. 25, 2017, provisional application No. 62/697,854, filed on Jul. 13, 2018, provisional application No. 62/907,300, filed on Sep. 27, 2019, provisional application No. 62/979,999, filed on Feb. 21, 2020, provisional application No. 62/986,461, filed on Mar. 6, 2020, provisional application No. 63/005,202, filed on Apr. 3, 2020.

(51) Int. Cl.
| | |
|---|---|
| *A61B 3/024* | (2006.01) |
| *A61B 3/032* | (2006.01) |
| *A61B 3/12* | (2006.01) |
| *A61F 9/08* | (2006.01) |
| *G16H 10/60* | (2018.01) |
| *G16H 30/20* | (2018.01) |
| *G16H 50/20* | (2018.01) |
| *G16Z 99/00* | (2019.01) |

(52) U.S. Cl.
CPC ............... *A61B 3/12* (2013.01); *G16H 10/60* (2018.01); *G16H 30/20* (2018.01); *G16H 50/20* (2018.01); *G16Z 99/00* (2019.02); *A61F 9/08* (2013.01)

(58) Field of Classification Search
CPC  A61B 3/024; A61B 3/032; A61B 3/12; A61F 9/08
USPC ......................................................... 351/224
See application file for complete search history.

(56) References Cited

U.S. PATENT DOCUMENTS

| | | | |
|---|---|---|---|
| 10,323,904 B1* | 6/2019 | Batten | ..................... F41G 3/145 |
| 2002/0063807 A1 | 5/2002 | Margulis | |
| 2003/0223038 A1 | 12/2003 | Alster et al. | |
| 2005/0036109 A1* | 2/2005 | Blum | .................. G02B 27/0172 351/159.03 |
| 2009/0218400 A1* | 9/2009 | Boss | ....................... F41G 3/142 235/404 |
| 2010/0011959 A1 | 1/2010 | Marra | |
| 2010/0149073 A1 | 6/2010 | Chaum et al. | |
| 2012/0206335 A1* | 8/2012 | Osterhout | ................ G06F 1/163 345/156 |
| 2013/0172902 A1 | 7/2013 | Lightcap et al. | |
| 2014/0094655 A1 | 4/2014 | Newman | |
| 2014/0160264 A1 | 6/2014 | Taylor et al. | |
| 2014/0275760 A1 | 9/2014 | Lee et al. | |
| 2014/0283429 A1* | 9/2014 | Sullivan | ..................... F41G 3/06 42/111 |
| 2016/0091968 A1 | 3/2016 | Angelo et al. | |
| 2016/0247418 A1 | 8/2016 | Folzenlogen et al. | |
| 2016/0252325 A1* | 9/2016 | Sammut | ..................... F41G 3/08 42/122 |
| 2016/0262608 A1 | 9/2016 | Krueger | |
| 2016/0270656 A1 | 9/2016 | Samec et al. | |
| 2017/0007351 A1 | 1/2017 | Yu | |
| 2017/0011706 A1 | 1/2017 | Namkung et al. | |
| 2017/0094167 A1 | 3/2017 | Riedel | |
| 2017/0293380 A1* | 10/2017 | Chauveau | ............. G06F 3/0362 |
| 2018/0116742 A1* | 5/2018 | Dell | ....................... A61B 34/20 |
| 2018/0250085 A1 | 9/2018 | Simi et al. | |
| 2019/0339528 A1 | 11/2019 | Freeman et al. | |
| 2019/0353457 A1* | 11/2019 | Northrup | .................. G01S 5/16 |
| 2019/0359351 A1 | 11/2019 | Fisher et al. | |
| 2020/0038120 A1 | 2/2020 | Ziraknejad et al. | |
| 2021/0149173 A1 | 5/2021 | Knoblich et al. | |

FOREIGN PATENT DOCUMENTS

| | | |
|---|---|---|
| KR | 1020130082637 | 7/2013 |
| WO | 2014140849 A2 | 9/2014 |
| WO | 2016133644 | 8/2016 |

(56) References Cited

FOREIGN PATENT DOCUMENTS

| WO | 2017064301 | 4/2017 |
|----|------------|--------|
| WO | 2018067611 | 4/2018 |

OTHER PUBLICATIONS

KIPO, "International Search Report", International PCT Application No. PCT/US21/30735, Feb. 24, 2022, Published in: WO.

* cited by examiner

AR/XR HEADSET FOR MILITARY MEDICAL TELEMEDICINE AND TARGET ACQUISITION

CROSS REFERENCE

This application is based on and claims priority to U.S. Provisional Patent Application No. 63/019,796 filed May 4, 2020. It is also a continuation-in-part of U.S. Patent Application Ser. No. 15/073,144 filed Mar. 17, 2016, which issued on May 1, 2018 as U.S. Pat. No. 9,955,862, U.S. patent application Ser. No. 15/940,561 filed Mar. 29, 2018, which issued on Oct. 30, 2018 as U.S. Pat. No. 10,111,583, U.S. patent application Ser. No. 16/173,719 filed Oct. 29, 2018, which issued as U.S. Pat. No. 10,874,297 on Dec. 29, 2020, U.S. patent application Ser. No. 17/137,069 filed Dec. 29, 2020, U.S. patent application Ser. No. 17/137,093 filed Dec. 29, 2020, and U.S. patent application Ser. No. 17/151,174 filed Jan. 17, 2021, all of which claim the benefit of U.S. Provisional Patent Application No. 62/134,422 filed Mar. 17, 2015; of U.S. patent application Ser. No. 15/962,661 filed Apr. 25, 2018, which claims the benefit of U.S. Provisional Patent Application No. 62/489,801 filed Apr. 25, 2017; of U.S. patent application Ser. No. 16/511,202 filed Jul. 15, 2019, which claims the benefit of U.S. Provisional Patent Application No. 62/697,854 filed Jul. 13, 2018; of U.S. patent application Ser. No. 16/511,451 filed Jul. 15, 2019; of U.S. patent application Ser. No. 17/034,944 filed Sep. 28, 2020, which claims the benefit of U.S. Provisional Patent Application No. 62/907,300 filed Sep. 27, 2019; and of U.S. patent application Ser. No. 17/182,022 filed Feb. 22, 2021, which claims the benefit of U.S. Provisional Patent Application No. 62/979,999 filed Feb. 21, 2020, U.S. Provisional Patent Application No. 62/986,461 filed Mar. 6, 2020, U.S. Provisional Patent Application No. 63/005,202 filed Apr. 3, 2020, and U.S. Provisional Patent Application No. 63/019,796 filed May 4, 2020. All are incorporated herein by reference.

COPYRIGHT NOTICE

A portion of this disclosure contains material that is subject to copyright or trademark protection. The copyright and trademark owner has no objection to the facsimile reproduction by anyone of this patent document as it appears in the U.S. Patent and Trademark Office, patent file or records, but reserves all copyrights whatsoever in the subject matter presented herein. The trademark names of the systems herein are those selected by the inventors but are not exclusive of names which could be used.

BACKGROUND OF THE INVENTION

Field of the Invention

This invention relates generally to AR/XR headsets, and more particularly, but not by way of limitation, to an augmented/extended reality (AXR) headset for medical field telemedicine and telesurgery assist, and for military target acquisition and aim for weapons and cameras.

Description of the Related Art

The use of AXR headset technologies may assist in future military conflicts as a telemedicine device for field medics. In the instance where a multi-domain battlefield exists where air superiority may not be assured, the military's current system of casualty evaluation may need to be replaced with a more sustained field care scenario that assumes an injured warfighter may be resuscitated and survive for several days while needing advanced medical care in the field. Thus, medical care in this forward battlefield scenario may require those that have limited medical training to provide care in a resource-scarce environment over lengthy periods of time. Providing rearward connected AXR headset systems to medics may help provide the care the injured warfighter through advanced telemedicine technologies, which provides for a field medic to have expert consultation from a highly technical specialist helps the field medic to provide skills beyond the capabilities of field generalists.

Further the AXR headset system may be used for target acquisition. When using a sight, even an electronic sight, on a rifle, the warfighter typically loses situational awareness and is somewhat contorted in physical posture.

The idea of attaching a reflector or reflex sight to a firearm has been around since the sight's invention in 1900. Many different types of reflector sights specifically designed for firearms have been marketed, some lit by batteries and some lit by ambient light. All of these previous sights had the reticle illumination drawback common with reflector sights small enough for a firearm: proper ambient lighting could not be depended on and incandescent light bulbs could drain a battery in a few hours.

Another method, the red dot method used a red aiming dot either generated by a laser or via a red plastic light pipe used to collect ambient light. Like other reflector sights, the collimated image of the red dot is truly parallax free only at infinity, with an error circle equal to the diameter of the collimating optics for any target at a finite distance. This is compensated for by keeping the dot in the middle of the optical window, i.e., sighting down the sight's optical axis.

Some manufacturers modify the focus of the LED/optical collimator combination, making models with the optical collimator set to focus the dot at a finite distance. These have a maximum amount of parallax due to eye movement, equal to the size of the optical window, at close range, diminishing to a minimal amount at the set distance, somewhere around a desired target range of 25 to 50 yards. A red dot sight is a common classification for a type of non-magnifying reflector or reflex sight for firearms, and other devices that require aiming, that gives the warfighter an aimpoint in the form of an illuminated red dot.

A standard design uses a red light-emitting diode (LED) at the focus of collimating optics, which generates a dot style illuminated reticle that stays in alignment with the weapon the sight is attached to regardless of eye position. In other words, it is nearly parallax free. They are considered to be fast-acquisition and easy-to-use gun sights for target shooting, hunting, and in police and military applications. Aside from firearm applications, they are also used on cameras and telescopes.

On cameras, they are used to photograph flying aircraft, birds in flight, and other distant, quickly moving subjects. Telescopes have a narrow field of view and therefore are often equipped with a secondary finder scope, such as a red dot sight.

There is growing demand on the part of armed and security forces for asymmetric combat capabilities and a tendency towards total battlefield digitization. This requires reinforcing expertise in low light levels (LLL) and infrared, in particular uncooled, detector technologies, multispectral cameras, and image processing and analysis, whether inhouse or with partners. The primary areas of focus are multispectral optronics, image processing, new-generation tactical drones, vibrating gyros, and micro-electromechanical systems (MEMS), applied to next-generation navigation systems for both military and civil applications. For example, this warfighter-oriented strategy led to the development of the digital target acquisition system herein.

Based on the foregoing, it is desirable to provide a sighting system that addresses the limitations of current sights while allowing new features to be realized.

SUMMARY OF THE INVENTION

In general, in a first aspect, the invention relates to the use of an augmented and extended reality AXR headset for remote medical diagnosis, and real-time surgery and injury care between a generalist, such as a field medic or surgeon and a more specialized expert like a sub-specialty surgeon, expert, or other healthcare specialists. When both the generalist and specialist are wearing a connected AXR headset system, both can see the actual injury, injury care or surgery, and the remote expert may provide enhanced care to a field care situation.

In another aspect of the invention an AXR headset may comprise a target acquisition and visualization system comprising an AXR headset and a digital sight capable of being mounted on a weapon, the digital sight in communication with the AXR headset. The digital sight may be an existing weapon sight with an additional digital camera added, or the digital sight may be a sighting module of a digital nature capable of sending target information to the AXR headset. In addition, in another embodiment of the invention, a trigger activation mechanism, such as an actuator, may be used to automatically fire the weapon according to the input and output of the digital target acquisition system (DTAS).

The communication between the DTAS and the AXR headset may be wired or wireless. The digital sight may have optical and/or digital zoom capabilities, and the zoom capabilities of the digital sight may be controlled by the AXR headset.

The system may further comprise computer vision artificial intelligence software enhancements. The computer vision artificial intelligence software enhancements may be capable of identifying visual elements at which munitions should intersect and identifying the precise timing of munition release.

The system may further comprise recording capabilities such that the system is capable of recording a feedback loop while identifying and acquiring a target and identifying where munitions hit the target and using the feedback loop to produce digital corrections in real-time. The system may further comprise an inertial measurement unit attached to the digital sight, where the inertial measurement unit is capable of pre-determining the moment when firing should begin and tracking the target for continued fire correction, as well as recording success rate, continuously learning, and adapting. The system may further comprise a gyro system capable of being attached to the weapon, where the gyro system is controlled by the AXR headset to lessen the impact of kickback and bring the weapon back in line with a previous sight or the previous sight plus an adjustment radii. The system may further comprise real-time eye-tracking embedded in the AXR headset, such that the system is capable of determining an area of interest based on eye-tracking. The AXR headset may comprise one or more forward and/or backward and/or upward mounted cameras. The AXR headset may have a latency of no greater than 20 ms from image acquisition to display output.

Figure 1:
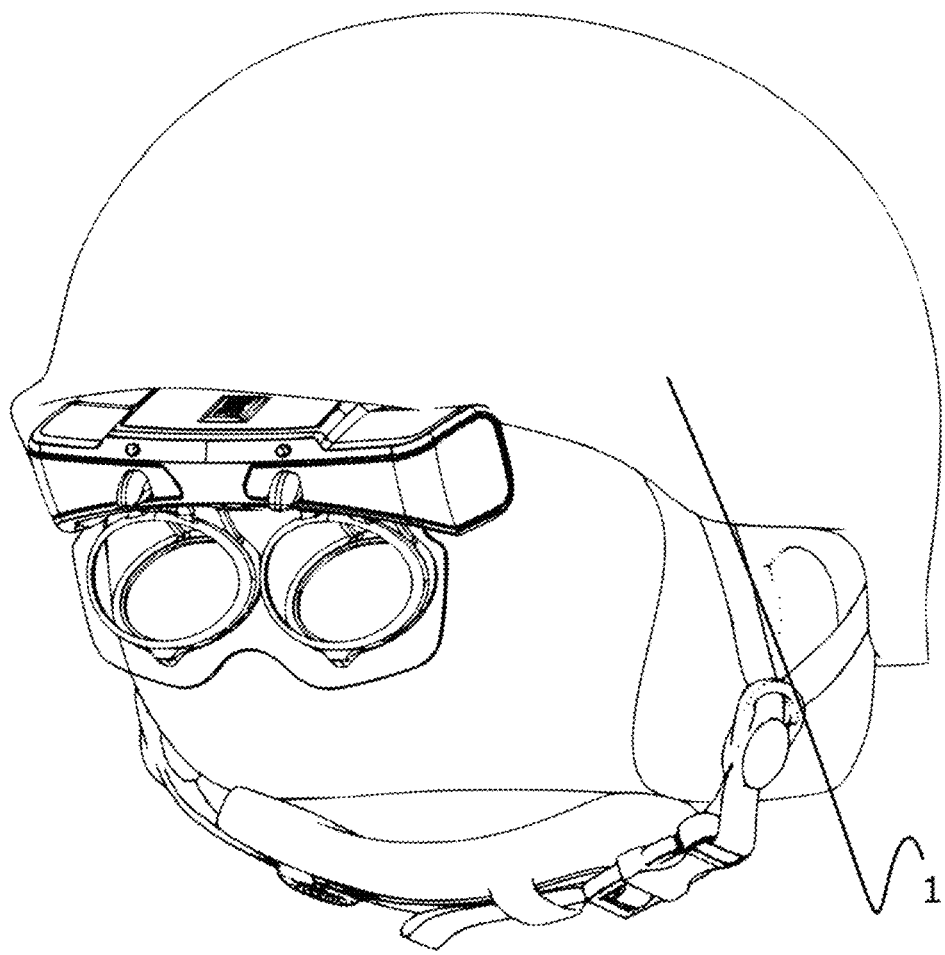
FIG. 1 is a diagrammatic illustration of the augmented reality headset with the virtual target acquisition imaging.

Other advantages and features will be apparent from the following description and from the claims.

DETAILED DESCRIPTION OF THE INVENTION

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

The AXR Headset System

"Augmented and Extended Reality" (AXR) is defined herein in its common scientific use, which may include an interactive experience typically in a see-through headset with lenses of a real-world environment where the objects that reside in the real world are enhanced by computer-generated perceptual images and information, sometimes across multiple sensory modalities, including visual, auditory, haptic technologies, somatosensory, and/or olfactory.

"Extended Reality" is defined in its common scientific use, which is typically an umbrella term encapsulating AXR (AR) and/or virtual reality (VR) and/or mixed reality (MR) and/or real reality (RR) and everything in between. It may also include combined environments and human-machine interactions generated by computer technology such as 6DoF and SLAM, and artificial intelligence (AI), including machine learning (ML), where the 'X' represents a variable for any current or future spatial computing technologies, including digital content of any sort; for instance, in the medical field, a 3D MRI or CT scan images or data visualizations, like patient vitals, superimposed or overlaid on an AXR headset in one of the several methods outlined herein.

"Artificial Intelligence" (AI), sometimes called "Machine Learning" (ML), is used herein in its common scientific meaning, including referring to the simulation of human intelligence in machines that are programmed to think like humans and mimic their actions and decisions. The term may also be applied to an AXR headset that exhibits traits associated with a human mind, such as learning and/or problem-solving. AI may enable AXR to interact with the physical environment in a multidimensional way. For instance, AI may permit object recognition and tracking, gestural input, eye-tracking, and voice command recognition to combine to let the warfighter manipulate 2D and 3D objects in virtual space with the warfighter's hands, eyes, and/or words.

The term "image(s)" or "virtual image(s)" or "imaging" or "virtual objects" or "AXR imaging" is defined for the purpose of this patent as visualization of either 2D images or video or 3D images or video. The definition also includes the concept that one or more 2D images can be viewed in stereoscopy to create one or more virtual 3D perspectives. Further included in the "image(s)" definition, herein, is the idea that AXR 3D models may be viewed as a single or series of 2D images, as in a still picture or video, or a single or series of stereoscopic 3D images, as in a 3D images or video. The 3D effect may be created in the AXR headset by using an off-set paired perspective of a 3D model. In addition, 3D models in AXR can be viewed from different perspectives by the warfighter or multiple warfighters can view the same image from multiple perspectives.

The term "wireless" as used herein means the electromagnetic transfer of information between two or more points which are not connected by an electrical conductor, or a communication by technologies, such as light, magnetic, or electric fields, or the use of sound. The term "wired" communication as used herein includes all methods of wireline communication including, but not limited to, directly connected devices, telephone networks, ethernet connections, cable networks, internet access, fiber-optic communications, and waveguide (electromagnetism) connections.

The following are sensing and control technologies which may be utilized by the AXR headset system:

"Six Degrees of Freedom" (6DoF) is defined herein in its common meaning, including the way virtual objects can be moved in virtual space in AR. There are six total degrees of freedom in placing virtual images in AR. Three (3) correspond to rotational movement around the x, y, and z axes, commonly termed pitch, yaw, and roll. The other three (3) correspond to translational movement along those axes, which can be thought of as moving forward or backward, moving left or right, and moving up or down.

"Inertial Measurement Units" is used herein in its common scientific meaning, including referencing devices for measuring rotational movements, such as an accelerometer, a gyroscope, and a magnetometer, all located within the AXR headset. These IMUs may measure the headset's velocity, orientation, and gravitational forces to infer rotational orientation and movement.

"Haptic technologies" is used herein in its common scientific meaning and is sometimes called kinaesthetic communication or 3D touch. It may also refer to any technology which may create an experience of touch by applying forces, vibrations, or motions to the warfighter or to an object. Haptics may enable warfighters to feel the sense of touch via vibrations of forced motion. Haptic technologies can be used to create virtual objects in a computer simulation or virtual space, or to control those virtual objects, and may be used to enhance remote control of machines and devices (telerobotics). Haptic devices may incorporate tactile sensors that measure forces exerted by the warfighter on the interface. This technology may employ touch sensors for control.

"Object Recognition" (OR) or "Object Identification" (OI) is used herein in its common scientific meaning, including a computer vision technique for identifying objects in images or videos. Object recognition may be a key output of deep learning and AI algorithms. When humans look at a photograph or watch a video, we can readily spot people, objects, scenes, and visual details. OR/OI does this from visual analysis based on a neural network algorithms reconciliation with pre-existing information.

"Simultaneous Localization and Mapping" (SLAM) is used herein in its common scientific meaning, including a technology that understands the physical world through a 3D grid of feature points. SLAM maps what the camera and sensors see in three dimensions with correct spatial information and distancing. This may make it possible for AXR applications to recognize RR 3D objects and scenes, as well as to instantly track motion in the RR, and to overlay digital interactive augmentations. SLAM incorporates the application of sensors sensing dept, time-of-flight, and creating a 3D grid. SLAM also incorporates infrared sensing and measurements.

"Gyro" or "Gyroscopic System" is used herein in its typical scientific meaning which is a device used for measuring or maintaining orientation and angular velocity. It is a spinning wheel or disc in which the axis of rotation (spin axis) is free to assume any orientation by itself. When rotating, the orientation of this axis is unaffected by tilting or rotation of the mounting, according to the conservation of angular momentum.

The AXR headset system may use SLAM, 6DoF, time-of-flight (ToF), and/or ultra-sonic transducer depth estimation or LIDAR to identify the exact position of the target. Alternatively, the system could use information provided externally in the form GPS or geographic coordinates.

The AXR system contains magnification and focusing system, and dual sensors for 3D viewing, software, algorithms and processing capability, including a model controller, computer vision technologies, and computer graphics technologies.

The micro-displays 44 may be organic light-emitting diodes (OLED or Organic LED), also known as organic electroluminescent (EL) diodes, which is a light-emitting diode in which the emissive electroluminescent layer is a film of organic compound that emits light in response to an electric current or LCD. This organic layer may be situated between two electrodes; typically, at least one of these electrodes is transparent. The micro-displays 44 of the system may each comprise a front plane and a semiconductor back plane manufactured by a silicone fab connecting the multiple front-plane screens.

When the micro-display emits 1,000 NITS, the eye-box value may be 300 to 500 NITS, depending on the image material. This may be adjustable by the warfighter. For reference, a TV is designed for 300 to 500 NITS, but a computer monitor is designed at only 200 NITS because it is assumed that you will be looking at it for hours on end and the desire is to reduce eye strain.

Figure 1A:
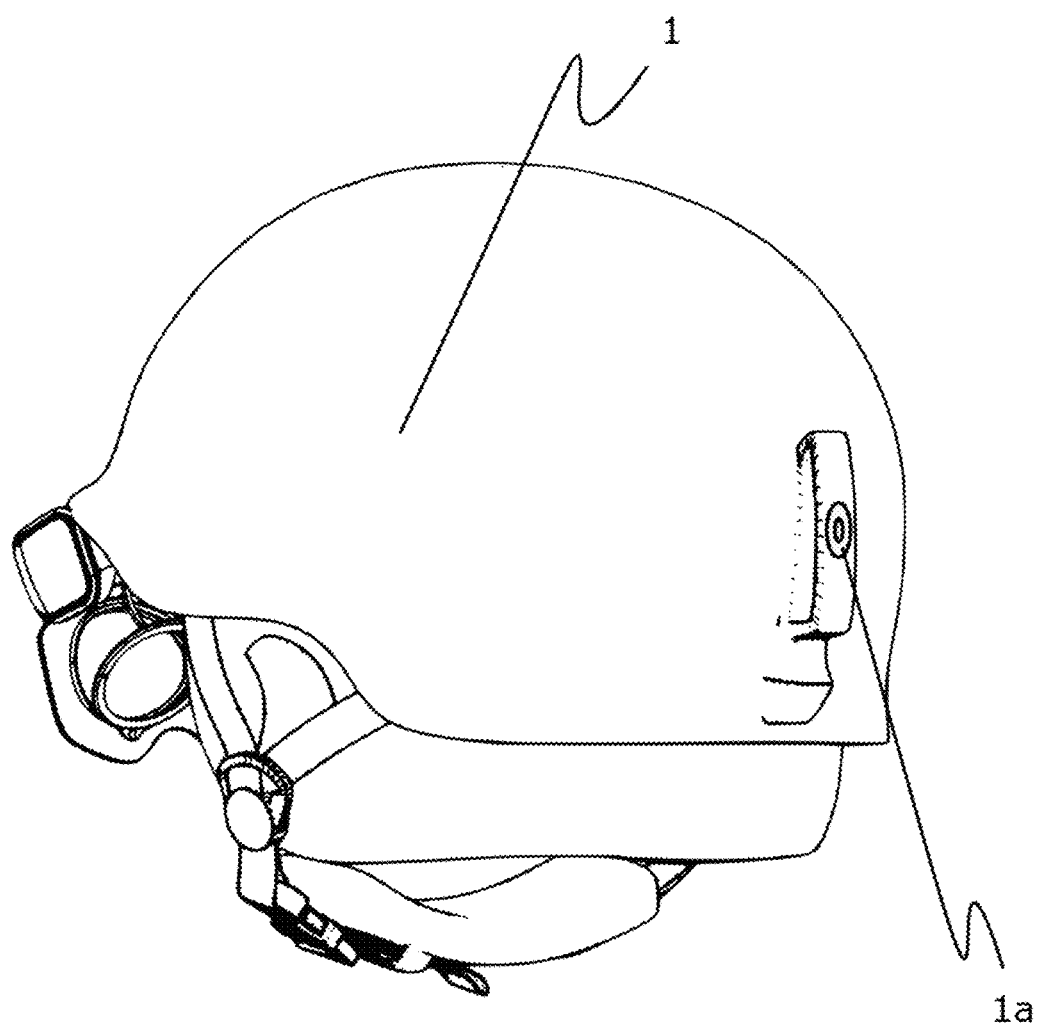
FIG. 1(a) is a diagrammatic illustration of the back view of the AXR headset with rear-facing threat alert camera.
Figure 3:
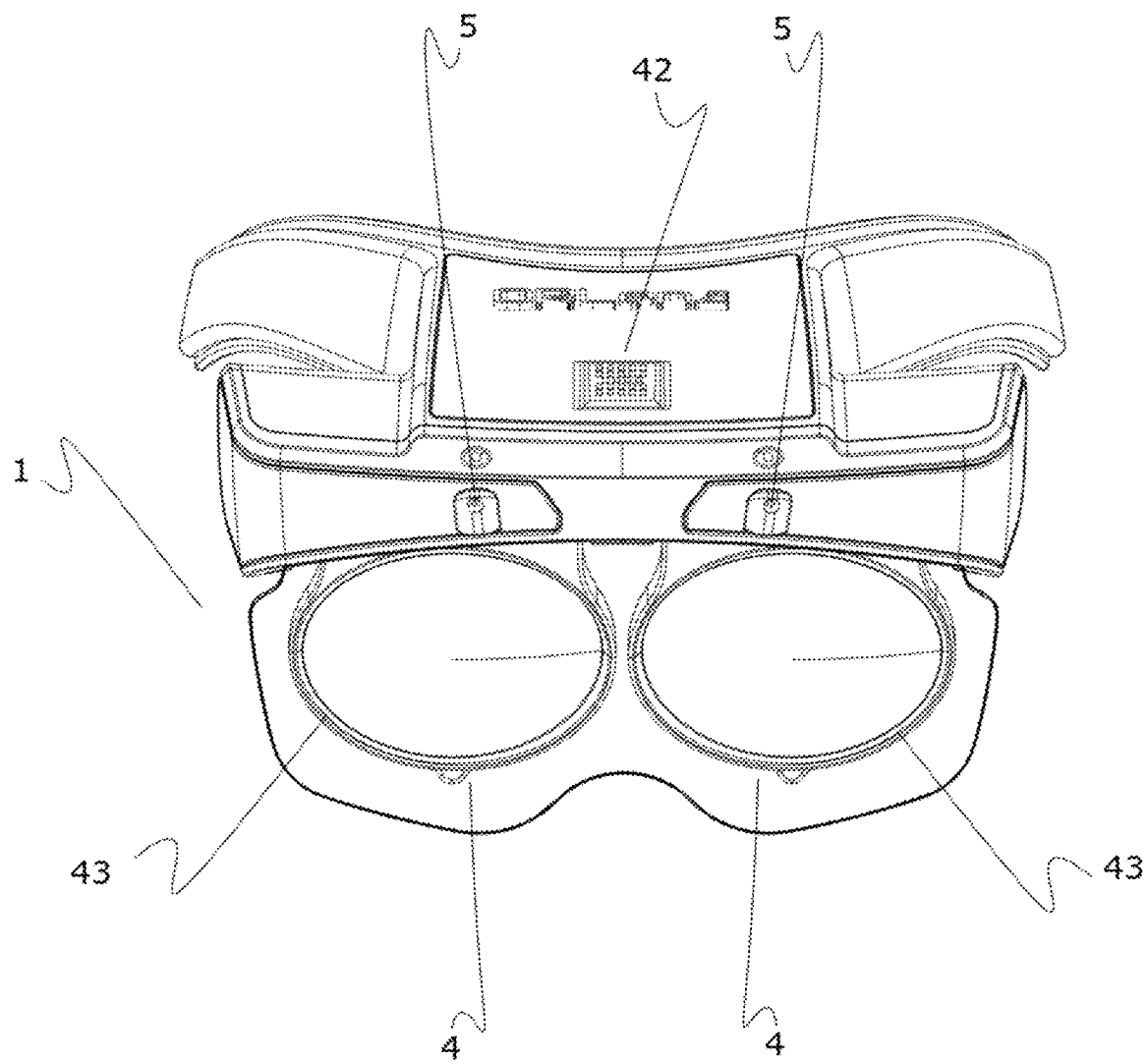
FIG. 3 is a front view of the AXR system headset without a helmet configuration.

In general, the AXR headset system invention relates to an augmented and extended reality digital target acquisition system may be either wired or typically the preferred wireless connection to the headset. The system may comprise a wearable device 1, such as a head mounted display (HMD) or glasses, that provides the warfighter with virtual reality (VR), AXR (AR), and/or mixed-extended reality (XR) for target visualization, as shown in FIG. 1A. Or it may comprise a system as shown in FIG. 3 with a larger battery box for longer use. This may allow the warfighter to access 2D or 3D imaging, magnification, virtual visualization, six-degrees of freedom (6DoF) image, and simultaneous localization and mapping (SLAM) management, and/or other images while still viewing real reality (RR) and thus maintaining a presence in the battlefield. The AXR headset control of the virtual world may include sensors including haptic sensors which may be worn on the hands and connected to the headset for coordinated control.

Figure 2:
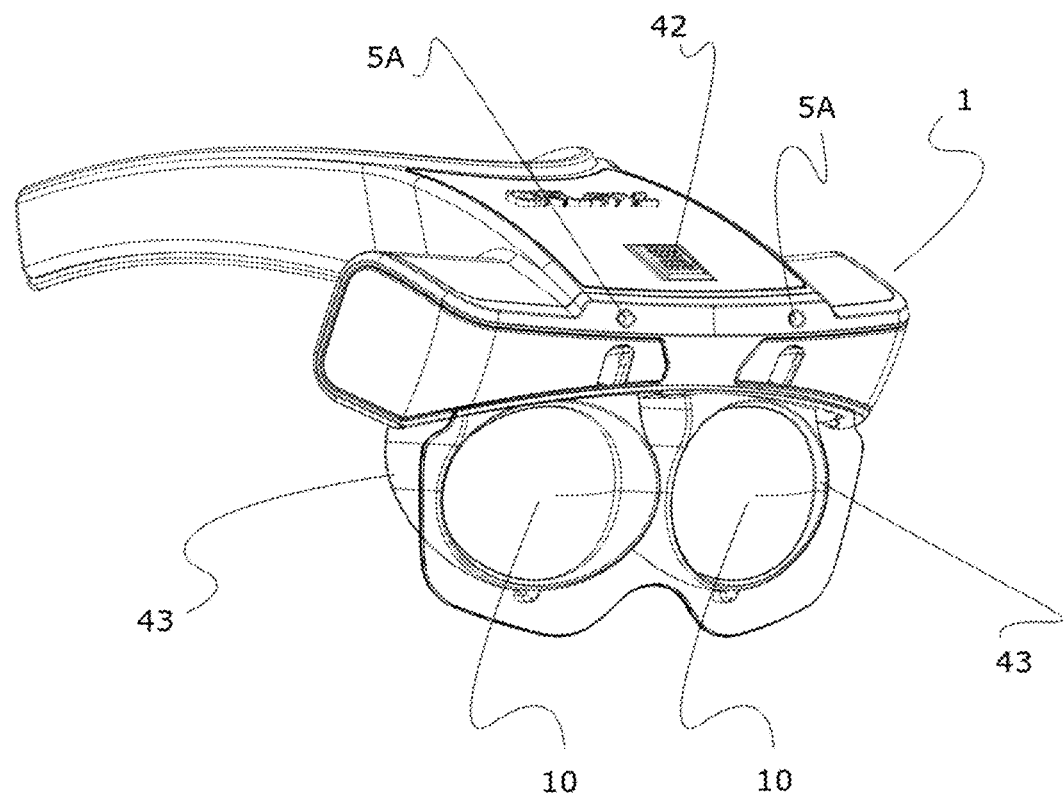
FIG. 2 is a perspective view of the AXR system headset without a helmet configuration.

The AXR headset system may comprise one or more micro-displays 44, a head-tracking subsystem (internal), an eye-tracking subsystem 4, and one or more cameras 5, all of which may be included on the wearable device 1. The system may further comprise one or more lenses 10, where the micro-displays 44 are capable of projecting images on the lenses 10, where the images may be reflected back to the warfighter's eyes. For example, as shown in FIGS. 1, 2 and 3, the wearable device 1 may be a head mounted display with a pair of lenses 10, one in front of each of the warfighter's eyes. One or more micro-displays 44 may be located above the warfighter's eyes and may be pointed toward the lenses 10. The two or more AXR cameras 5 may be 4K or higher each and may provide image input, while the head-tracking subsystem 3 and the eye-tracking subsystem 4 may provide positional input, allowing the system to project the desired images to the desired location for the warfighter to view the images. Additional image input may be provided from other sources such as SLAM or other sensing cameras 5A. The AXR is connected to the target acquisition system and receives and transmits to the system for target visualization and commands back to the system.

All components may be controlled by a CPU and enabled by a GPU and one or more digital signal processors, cables, and battery source, which may be located on the wearable device 1 or remotely. Other components may include additional central processing units, one or more graphics processing units, one or more digital signal processors, firmware, hardware, software, and/or memory components, as well as other desired components, including a non-transitory model view controller. The high-level components may control the features and functions of the AXR headset 1, including, but not limited to, its cameras 5, micro-displays 44, lenses 10, sensors, communications, and subsystems.

Among virtual image display solutions for AXR viewing are catadioptric optics, which are preferred in that they employ a partially transmissive curved mirror for directing image-bearing light to the viewer's eye and a partially reflective beam splitter for combining light generated at a 2D display with the real-world visible scene, which forms a superior 3D image and holographic images when viewed binocularly.

The headset may be wireless or wired. If wireless, the wireless module antenna may be connected to the main circuit board inside the headset and may radiate RF to the outside world through the WiFi, cellular, or 5G antennae 42.

The AXR headset may contain a small worm gear or similar device connected to the two lens frames 43, which may move closer and farther, approximately 5 mm, in order to adjust for interpupillary distance (IPD) for each person. This may be accomplished by the worm gear being connected to a spindle gear threaded on both ends, which may connect to the lens frames, which may be on a track that permits them this measure of movement. A remote Bluetooth connection may be housed in the charging station drawers, where it can automatically adjust based on the information preprogrammed into the AXR headset system controller according to each warfighter's IPD or can be accomplished manually through a small Bluetooth handheld device housed in each drawer and independently connected and secured to each device.

Figure 7:
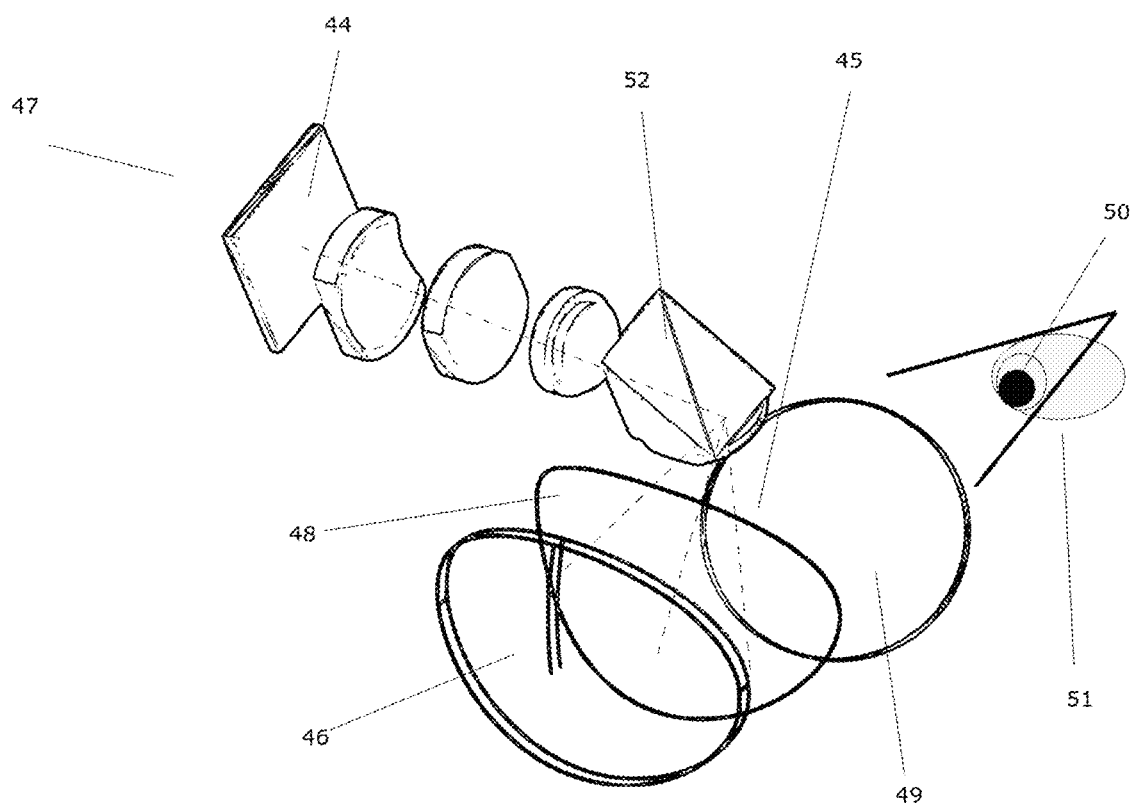
FIG. 7 is a break-out of the near-eye pupil-forming catadioptric optical engine in the AXR headset.

One such AXR headset, as shown in FIG. 7 and which may produce the best results for target, is an axially symmetric near-eye pupil-forming catadioptric wearable AXR display apparatus comprising:

(i) relay of the image generator 44 to form a curved intermediate image 45 as a conjugate image. As a type of "aerial" image, intermediate image 45 may be formed in air, serving as the optical "object" for forming the virtual image. Intermediate image 45 may be formed along the curved focal surface of curved mirror 46, with the approximate aerial position shown by a dashed line in FIG. 7.

(ii) an optical relay 47, with particular structure as described in more detail subsequently, may conjugate the image formed from image generator 44 to the curved intermediate image 45 along the focal surface.

(iii) a curved mirror 46 may be partially transmissive, such as between about 30% to 70% transmissive, for example, allowing visibility of the real-world object scene to the viewer. A nominal transmission range of 50 to 70% may be useful in many applications and the see-through may be increased with the use of brighter imaging source such as an LCD or other micro display.

(iv) a beam splitter 49 is used to reflect light from the relay 47 to the curved mirror 46 and may be an unpolarized or polarized beam splitter. It may transmit light from both the real reality external to the viewer and the virtual reality reflected off the surface of curved lens 46.

(v) use of a cylindrically curved quarter-wave plate (QWP) between mirror 48 and beam splitter 49. Curvature of this element may help to reduce variations of the retardation imparted to the image-bearing light by the QWP over the field of view.

(vi) large exit pupil 50. System optics can form a 10 mm exit pupil at the viewer's eye-box for eye 51. Forming a suitably sized pupil for the viewer may help to provide an eye box of reasonable dimensions to allow eye movement, without noticeable vignetting. Also, an enlarged eye box may permit the headset to move or slip without noticeable degradation of the viewed image(s). The apparatus may not need to provide pupil expansion, such as is used in existing wearable display apparatus, but may use pupil-forming optics for improved efficiency and brightness, as well as for improved image resolution.

Significantly, the eyes of the viewer may clearly see and be seen by others, with minimal impediment from the beam splitter and curved mirror optics that provide the electronically generated virtual image.

With the optical arrangement shown, the aperture stop AS may lie within prism 52 of the image relay, along or near the fold surface that is provided. This arrangement may be advantageous for component packaging and spacing, allowing the prism to be reduced in size over other configurations using a folding prism.

The given design may allow an FOV along the horizontal (x) axis, the axis parallel to a line between left and right pupils of the viewer's eyes, of greater than 50 degrees. The FOV aspect ratio (horizontal:vertical) may equal or exceed 1.5. Digital correction may not be needed for distortion or lateral color.

According to an embodiment, curved reflector 46 may have a conic surface shape. The conic shape is advantaged, in the embodiment shown herein, helping to control chief ray angles, thus correcting for distortion. Depending on whether or not polarization is used for configuring light paths, beam splitter 49 can be either an unpolarized beam splitter or a polarizing beam splitter. Beam splitter 49 can be, for example, a wire grid polarization beam splitter as shown in FIG. 7.

Figure 5:
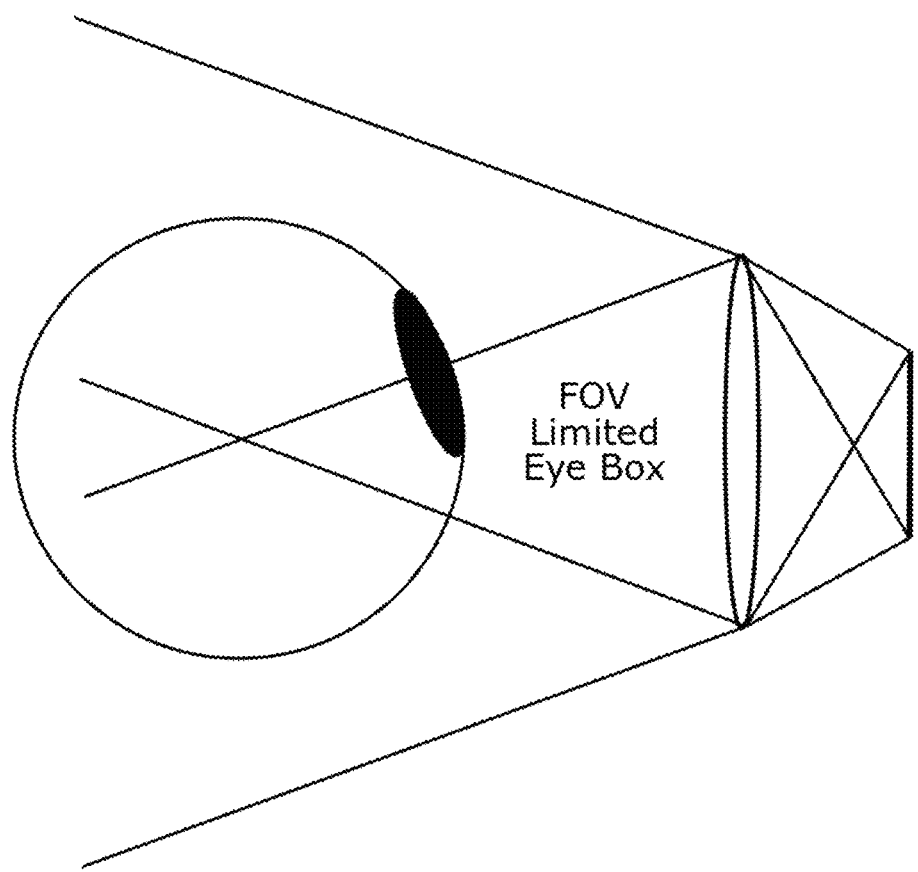
FIG. 5 is a diagrammatic illustration of an eye box.

The AXR system design may create a large eye box for the warfighter, as shown in FIG. 5. The eye box of any AXR or VR system may be crucial as it may serve as the connection between the device and the warfighter. The eye box of the system may be large enough to provide comfortable viewing of the full field of vision with the highest resolution and contrast even if the headset moves while wearing. Further, the eye relief of the system may be large enough to account for distance of the system to the warfighter's eye, including allowances for brow size and how deep-set the warfighter's eyes are, as well as clearance for eyeglasses. Thus, the near eye pupil forming catadioptric optical system FIG. 7 described herein is able to provide an image free of the type of chromatic aberrations typically found in a pupil expanding waveguide technology while maintaining a sufficient eyebox with good eye relief. The eye relief of a typical optical instrument is the distance from the last surface of an eyepiece within which the warfighter's eye can obtain a full viewing angle. If a viewer's eye is outside this distance, a reduced field of view may be obtained. The eye box refers to the range of movement of the eye in which the system maintains an adequate image. Thus, the smaller eye box of previous VR systems is inferior to the large eye box of the current system.

The AXR system may be capable of allowing the warfighter's eye to rotate in order to view off axis field angles while still maintaining high resolution, either AXR or RR, at approximately 50 pixels per degree. The optical engine in the system may accommodate not only large field of vision eye rotation, but also a translation of rotation of the pupil due to the fact that, in reality, the eye rotates about a point that is 10 mm behind the pupil, where the fovea actually exists. The optical engine may provide a virtually no-chromatic distortion display providing resolution of 56-60 pixels per degree. The optical engine may use an aspheric catadioptric off-axis engine. The asphere's more complex surface profile may reduce or eliminate spherical aberration and also reduce other optical aberrations such as astigmatism, compared to a simple lens. A single aspheric lens may be capable of replacing a much more complex multi-lens system when used in combination with an ellipse reflecting lens collector. The resulting device may be smaller, lighter, and less expensive than a multi-lens design. Aspheric elements may be used in the lenses to reduce aberrations, and in combination with reflective elements (catadioptric systems) such as the aspherical Schmidt corrector plate used in the Schmidt cameras and the Schmidt-Cassegrain telescopes or ellipse collector optical cut.

Features of the AXR optical engine may include microdisplay lens correction, optical collimators in more than one place, reflective lens correction to adjust the focal point for near eye projection, with dynamic opacity to compensate for brightness overcoming light loss, keystoning software distortion correction, IPD mechanical and/or software adjustment per person, and an off-axis, semi-spherical (elliptical) combiner in the inner portion of the lens.

Figure 8:
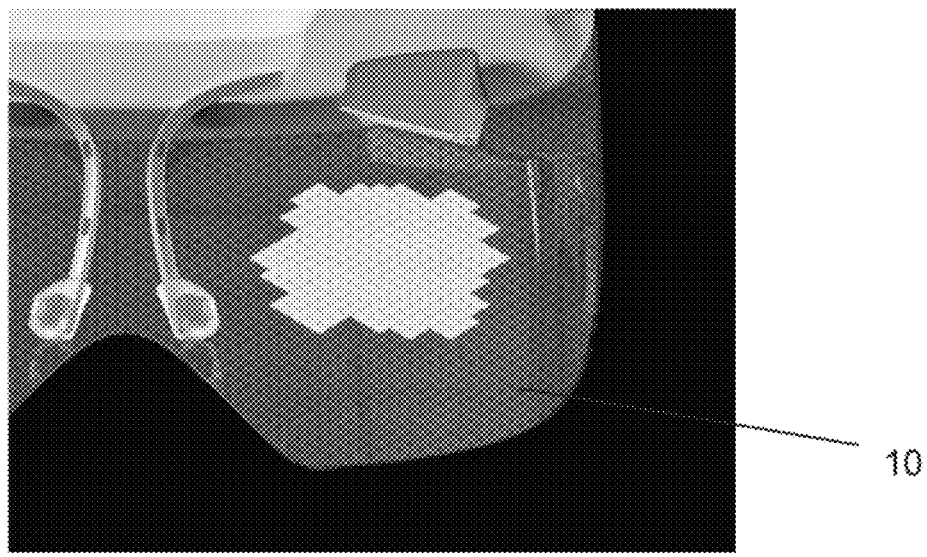
FIG. 8 is a close-up view of the dynamic opacity and the rotating articulation of the dual headset cameras up to 90 degrees.
Figure 8:
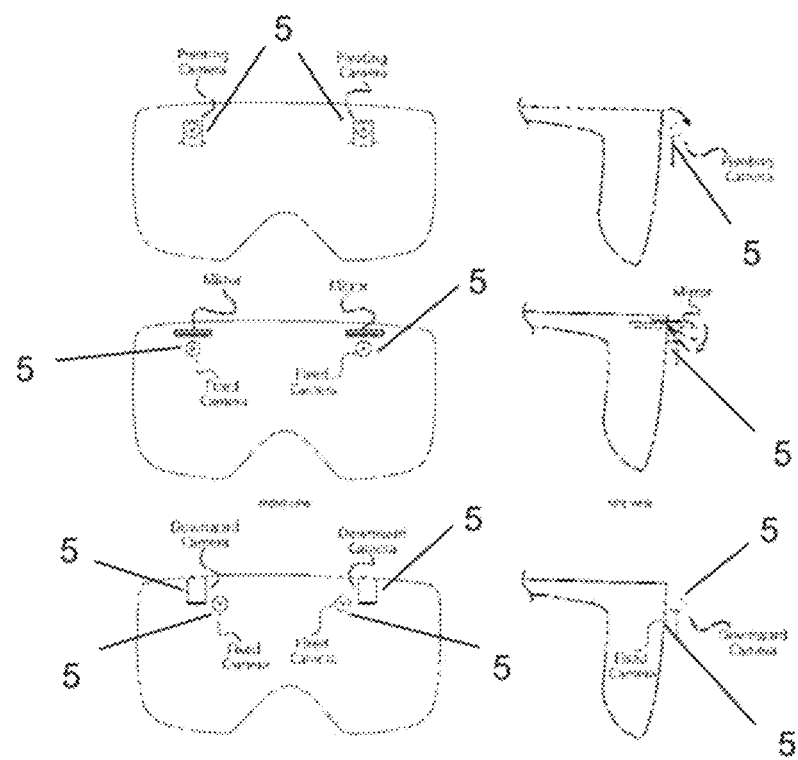

The dynamic opacity subsystem that allows the system to function as a true AXR system may be provided by a multilayered lens 10, which may be part of the wearable device 1. Typically, when using a reflected image on a see-through lens in sunlight or bright light conditions, the reflected image can be washed out. Other systems solve this problem with dark lenses. Having the lens shaded all the time, however, makes the wearer vulnerable to falling or tripping over unseen obstacles. The dynamic opacity of the lens 10 of the current system, however, may only obscure that portion of the lens 10 where the eyes are viewing the AXR image as alpha matte composites, meaning the combining of several images from different sources into a single image. FIG. 8 illustrates the dynamic opacity of the present system.

The system may utilize alpha matte software that works in conjunction with eye-tracking technology and software to map the warfighter's eye gaze and adjust not only the image, but also move or vary the opacity of the exterior of the lens 10 where the eyes are gazing, and the image is projected. In addition, the software may automatically or manually adjust the opaqueness of the alpha matte display up or down to meet ambient lighting conditions.

Figure 4:
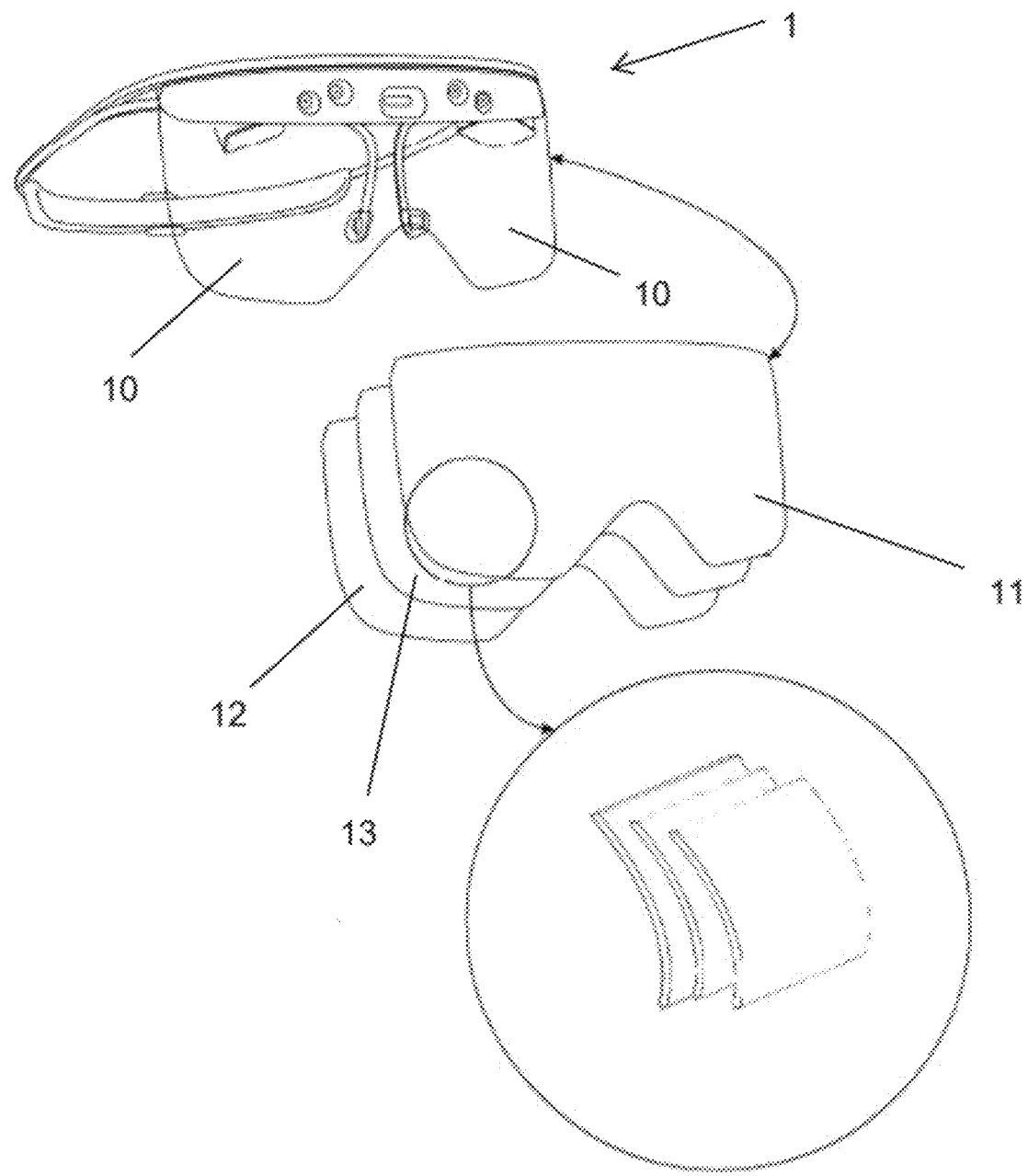
FIG. 4 is an exploded view of the lenses and optical engine.

The lens 10 may have multiple layers, as shown in FIG. 4, with dynamic opacity provided on the outer layer 11, furthest from the warfighter's eye. This layer 11 may be pixelated, which may permit the system to create a shadow or mirrored image of whatever virtual image is being displayed. This may provide a backdrop for the virtual image, blocking out light that might otherwise wash out the image. The remainder of the layer 11, where the image is not being displayed, may remain clear. Alternately, all of the pixels of the layer 11 may be activated, making the layer 11 fully obscure and blocking out the RR. This may allow the warfighter to use the system as a VR-type headset, but with the ability to see his or her hands to pick up tools and instruments in the periphery of the glasses where the lens does not obscure the RR vision. Thus, warfighters who are not presently in danger and do not need a view of the active battlefield can choose to engage the dynamic opacity via voice command and make the system more like a VR headset, blocking out the view through the lens 10 behind the AXR image or video when ultra-concentration is needed. At other times, the warfighter can choose to make the dynamic opacity off or clear in the portion of the lens where there is no reflected image, to use the system in normal mode, where only the AXR image is shadowed from the back. The dynamic opacity of the lens 10 may provide a buffer between the displayed image and exterior light, giving the AXR image greater brightness to the eye. The system may allow the dynamic opacity to be enabled automatically, under pre-set conditions, manually, or with voice, gesture, or eye-tracking command.

In this fashion, the system may give the warfighter the highest RR visibility, and the added benefit of both AR and VR, so that the best of both types of altered reality is provided.

The layer 11 may comprise a plurality of pixels of cholesteric liquid crystal, each of which may be independently capable of becoming clear or opaque, or in between, as desired. In other words, the layer 11 may use electrically switchable suspended-particle smart glass based on the chiral-numatics properties of certain liquid crystals, which may not require a polarizer to achieve the alpha matte or opaqueness. The dynamic opacity, since it does not have to rely on a polarization layer, may provide gradation from and including zero to 100 percent, while it is a generally accepted scientific fact that LDC technology with polarizers can only become approximately 50% clear. This is because a system using embedded polarizers can never become 100% clear.

In suspended-particle devices (SPDs), like the layer 11, a thin film laminate of rod-like nano-scale particles may be suspended in a liquid and placed between two pieces of glass or plastic or attached to one layer without polarization or back-plane. When no voltage is applied, the suspended particles may be randomly organized, thus blocking, and absorbing light. When voltage is applied, the suspended particles may align and let light pass. This dynamic opacity technology is bi-stable and is therefore highly energy efficient because the cholesteric liquid crystals do not need power to maintain a selected state like most LCD technologies, which use twisted-numatics and always need power to maintain each level of a twisted-numatic state.

The lens 10 may further comprise a reflective layer 12, which may be a lens or a coating. The reflective layer 12 may be located closest to the warfighter's eye and may be the surface upon which images projected by the micro-displays 44 for reflection back to the warfighter's eyes. An anti-reflective layer 13 may be positioned next and may be a layer or optical coating that may prevent unwanted artifacts, such as ghosting. The lens 10 may further comprise one or more collimators 14. The collimator 14 may be a separate layer included in the lens 10; additionally, or alternately, layer 11 or layer 12 may have aspects of a collimator, and thus may function as the collimator 14; additionally, or alternately, the collimator 14 may be a separate lens located between the micro-displays 44 and the reflective layer 12. The collimator 14 may be capable of concentrating rays from the micro-displays 44 in the eye box while utilizing less resolution in the periphery for an overall highest resolution and field of vision.

In one embodiment, the lens 10 may have at least three layers, including a polarized optical coating layer 12 applied to the inner surface to induce reflection and improve the contrast by eliminating stray light. This portion may contain the semi-spherical (elliptical) combiner. The middle layer may include polarization to create a perceived black. The outer layer 12 may include the dynamic opacity, which may be a pixelated layer controllable by software which induces a shadowing over the same area as the reflected AXR image for enhanced viewing even in bright light settings.

Thus, in addition to considerations of brightness, one must consider the imposition of an electronic darkening of the entire lens or electronic darkening of just the area in which the virtual image is contained pixel by pixel. This idea has been called dynamic opacity, which, when added to the optical engine, may also provide additional brightness to the AXR image by electronically darkening the RR around or behind the virtual image. By making the real world (RR) behind the AXR (AR) image on a gradient from 1% to 100% opaque, the dynamic opacity may provide an even greater luminance referred to the eye.

Alternatively, a chemical photo lens may be used as the external lens which can turn darker by exposure to light independently from electronic activation. Such a light-responsive lens begins to darken when exposed to UV rays (in both direct and indirect light) and then fades back to clear indoors with the level of darkness and speed of transition depend on the level of UV exposure and temperature.

The AXR system may be capable of displaying both real reality and computer-generated images (CG or CGI) or computer captured and manipulated images (CMI), effectively creating the illusion of AXR. In this context, CMI may mean previously recorded, captured, or created images or video from a different reality than the RR displayed in the AXR headset. Additionally, or alternately, the system may be capable of functioning as a "heads-up" system, allowing the warfighter to look at the images on the micro-displays or look beyond the display to the larger environment of the active battlefield and activity. Thus, the AXR system may provide a full field of vision, unlike existing systems. Specifically, for example, the micro-displays 2 may provide a wide field of vision of, for instance, 120 degrees, namely 60 degrees horizontal and 36 degrees vertically or more degrees in each eye, or other desired field of vision. This may allow a high angular resolution of 60 pixels per degree in the eye box, which is the highest resolution the eye can distinguish at 20/20. Humans have a slightly over 210-degree forward-facing arc of their visual field. The cameras 5 of the system may capture all or most of the human forward-facing degrees, when needed. Correspondingly, the warfighter may view 120 degrees field-of-view (FOV) of AXR through the AXR cameras 5 and 210 degrees of RR with the system functioning as a heads-up display (HUD). This field of vision may actually be even larger from a practical standpoint as the warfighter may, for example, look down at his or her hands, which are outside the AR/RR presented field of vision. The availability of viewing the RR environment may be important to a warfighter when he or she is trying to unfocus from the virtual image and look at the RR, for instance to load or re-load his weapon.

Figure 6:
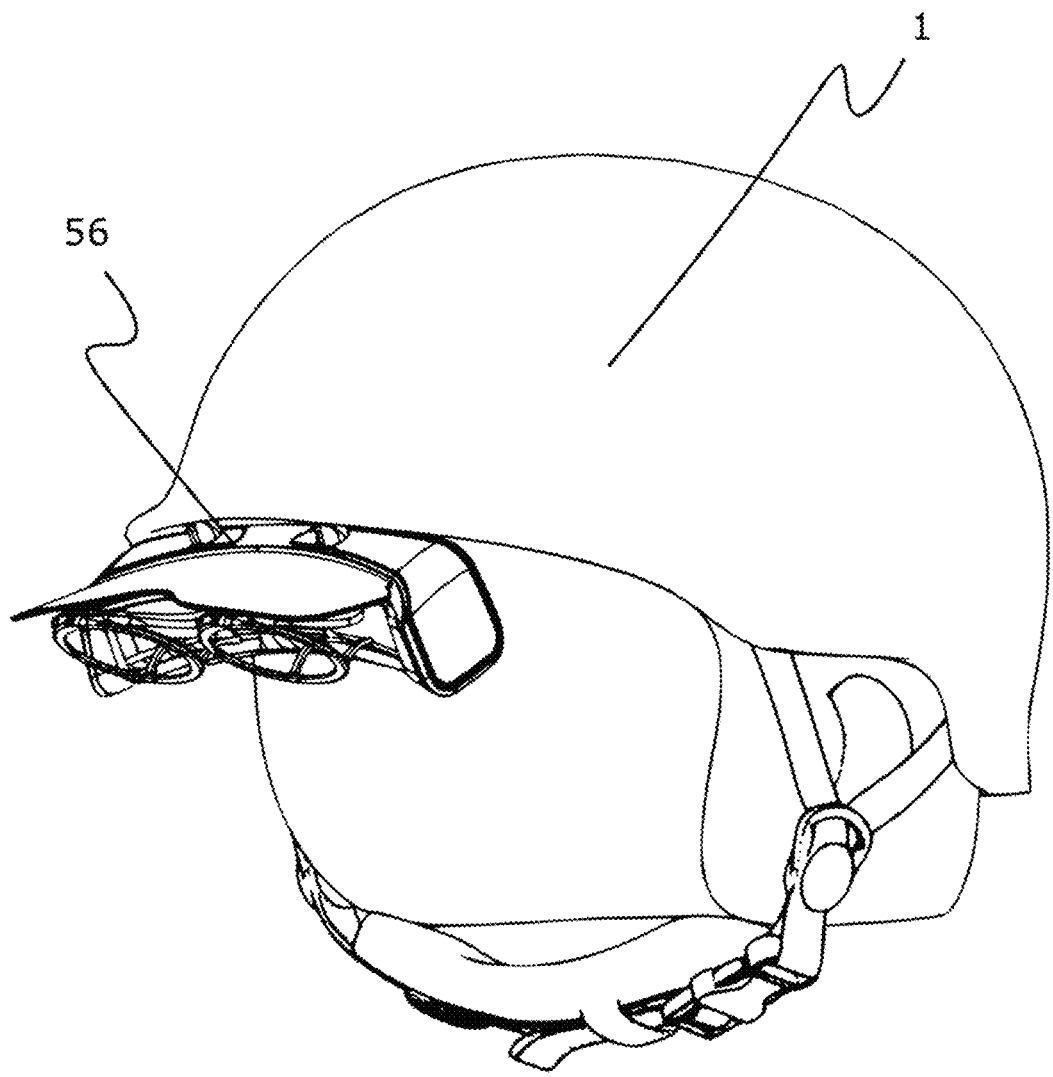
FIG. 6 is a diagrammatic illustration of the AXR visor flipped up and out of the way of the war fighters straight ahead view.

In one embodiment, the AXR Headset 1 may have a visor design 56, which may be open, or raised, and provide RR access to the eye, while when lowered both peripheral and downward viewing is available beyond the lens. The system may include a clip-on corrective lens that is capable of being clipped on at the open portion of the lens for forward-looking application or attached to the bottom of the lens so that warfighters with presbyopia can have their own prescription attached to the lens, such that when viewing combat weapons, tools or other items, their own prescription is included in the view. The visor may even be cantilevered over the head, or away from the head, if necessary, in emergency situations or off use times, in order to provide the warfighter with an opportunity to still wear the wearable device 1, but have the visor be out of view, as shown in FIG. 6.

The AXR cameras 5 may be two on-board 4K or higher resolution cameras and may, as noted above, capture a wide field-of-view, such as 180 to 210 degrees forward-facing vision. This oversampling of the field of vision may then be stored per frame and used in conjunction with the eye-tracking subsystem 4 to present the actual field of vision depending on the warfighter's gaze. In this fashion, the system may use images from the entirety of the 180 degrees captured or a reduced sample of the entire captured camera's FOV. The reduced sample may be based on eye-tracking and eye-gaze correspondently. As the system's eye-tracking follows the eye of the warfighter as his or her eyes move, the system may be able to provide a subset of imagery from the fully captured 200 or more degrees.

The two AXR headset cameras, as shown in FIG. 8, may be rotated up to 90 degrees on axis by voice command or virtual menu, or other control mechanism, which permits a warfighter to look straight ahead with an ergonomic posture, moving and adjusting as necessary, while the cameras pivot to show a surgery view of a patient on a gurney between 60 to 90 degrees.

The Connectivity Subsystem and Remote Medical Assist.

The wearable device 1 and 23 may be lightweight and may be wireless. One of the ways to reduce weight is to have only the cameras, a battery, and sensors in the headset 1 and 23 with connectors to a WiGig®/60 GHz modem using the fastest wireless protocol available, such as the IEEE 802.11ay protocol. Another embodiment places the intelligence in the headset 1, such as a Qualcomm® XR-2 chipset, and have the chipset circuit board be connected to a 60 GHz modem to send/receive streaming video to/from another WiGig connected location, In the case where the AXR headset receives video feed from such an outside source or system, such as a "One Pass Drone" either a wireless or satellite connection can be made with an alternative satellite modem on the warfighter or in the AXR headset. The AXR headset system may have a wireless transceiver mounted in one or more places which may send and receive wireless information from other sources, including another AXR headset system.

While Wi-Fi IEEE 802.11 may work, the best method would be to use a method so that uncompressed video can be sent from any image processing system to the AXR headset. In the preferred embodiment, a digital buffer would be acquired from the camera sensor as translated and augmented with the extra overlay information, if applicable, by the computer controller system, then the digital buffer is transmitted uncompressed to receiver, which may be in the AXR headset. When the uncompressed data and buffer is received by the receiving system it is then translated to a pixelized image as a sequence of the streaming video. In the event of a problematic transmission where the checksum is off, then that frame would not be displayed. In addition, the program may freeze any buffered frame for hold until a valid frame was received.

The use of these wireless technologies may in virtual medical field assist (VMFA) to assist medical a forward battlefield scenario which may require those that have limited medically training service personnel, such as a field medic to provide care in a resource-scarce environment over lengthy periods of time. Thus, providing AXR headset systems to medics with wireless or satellite connectivity, including but not limited to 5G MEC environments, may help provide the care the injured warfighter through advanced telemedicine technologies, which provide expert consultation for highly technical surgical skills beyond the capabilities of field generalists, which can be accomplished with the AXR headset system and connectivity. Due to the advanced capabilities of the AXR headset to capture, send, and receive 3D information, field trauma surgery could be performed with a remote reward healthcare specialist in consultation with the field medic through telemonitoring.

In addition, the AXR headset forward facing cameras may articulate to rotate downward to a position which may be up to 90 degrees from the plane of the front of the AXR headset. In this fashion, instead of a field medic having to focus downward or wear loops, which causes the user to put his chin on his chest throughout the assistance to the injured warfighter surgery or care, the AXR cameras tilt and to the injury and surgery site, leaving the field medic with a more ergonomic and comfortable posture and one where he can still see any movement or action on the battlefield.

In this fashion the AXR headset system may be used as a telemedicine technology for tele-mentoring a field medic or other on-site battlefield service person in order to allow a remote specialist, subspecialty surgeon, or healthcare provider to participate and provide surgical mentoring to an on-site field medic, or even to a battlefield hospital surgeon. The AXR headset system permits the specialists, subspecialty surgeon, or other healthcare provider to see the field condition and warfighter's injuries, and the actions of the field medic, or in the case of a battlefield hospital the operating room table, the hands of the surgeon and the surgical field, and provides a continuous two-way audio and video feed.

Figure 9:
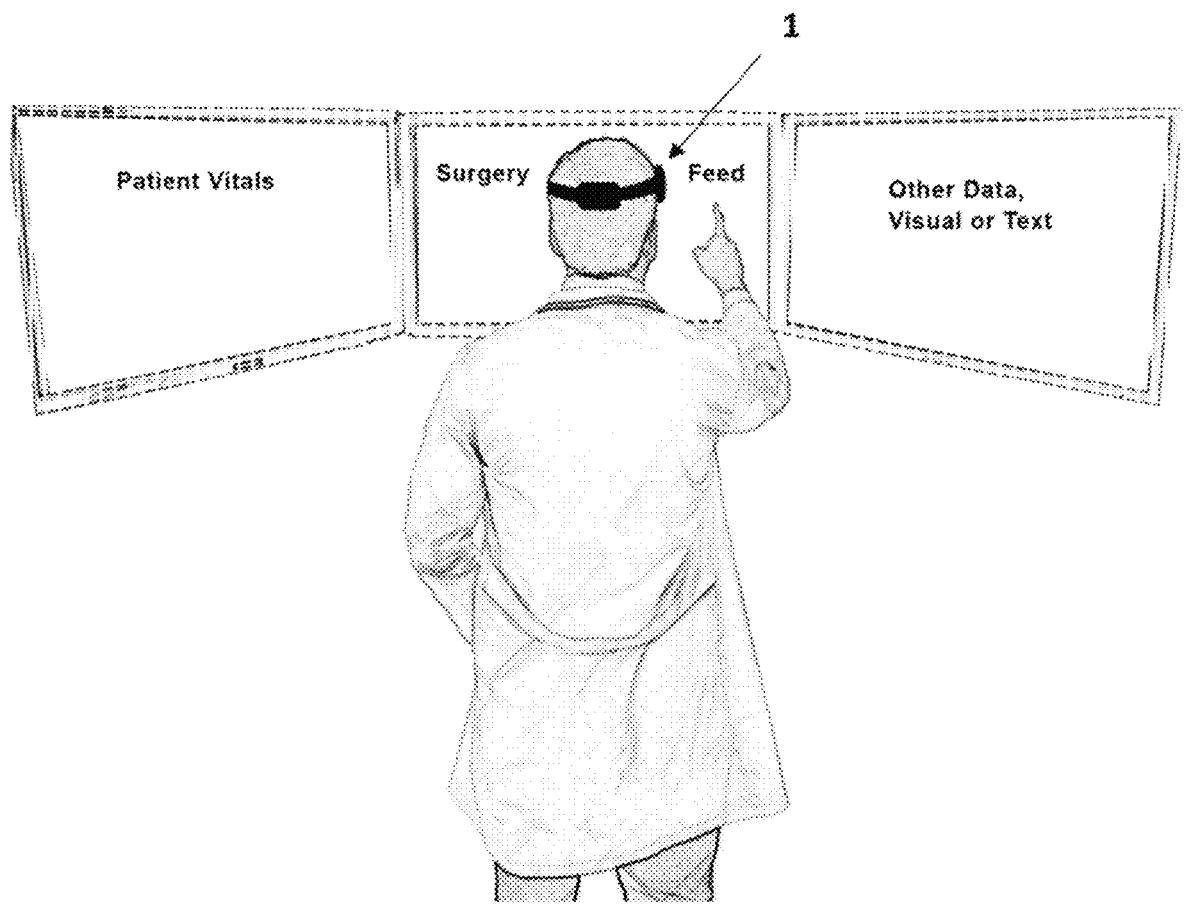
FIG. 9 is a back view of a person wearing the AXR headset, illustrating different views presented by the virtual overlay as seen virtually in the AXR headset.

As shown in FIG. 9, the AXR headset may be capable of virtual overlays placed either over either the field medic or specialist's AXR camera feed of the injured warfighter or in some quadrant or where he must turn his head or eyes to see the overlay. The overlay could be information fed from the specialist which may include a tutorial or anatomical information which would assist the field medic in his efforts. Conversely, the healthcare specialist also wearing a connected AXR headset can see exactly what is happening as the field medic renders aid and can thereby assist and improve the outcome by addition the specialist's real-time expertise seeing exactly what is going on in the field with the injured warfighter. The virtual overlay may include images, instructions, tutorials, pictures, videos, MRI's, CT scans, and the like to assist the field medic. This information may be visible upon voice command of the field medic or specialist, and the system may provide the user the option of displaying information at the bottom, side, or top of the AXR lens view or in a quadrant affixed by a fiducial marker, where the field medic or specialists would turn head or eyes to see the overlayed images and information.

Figure 10:
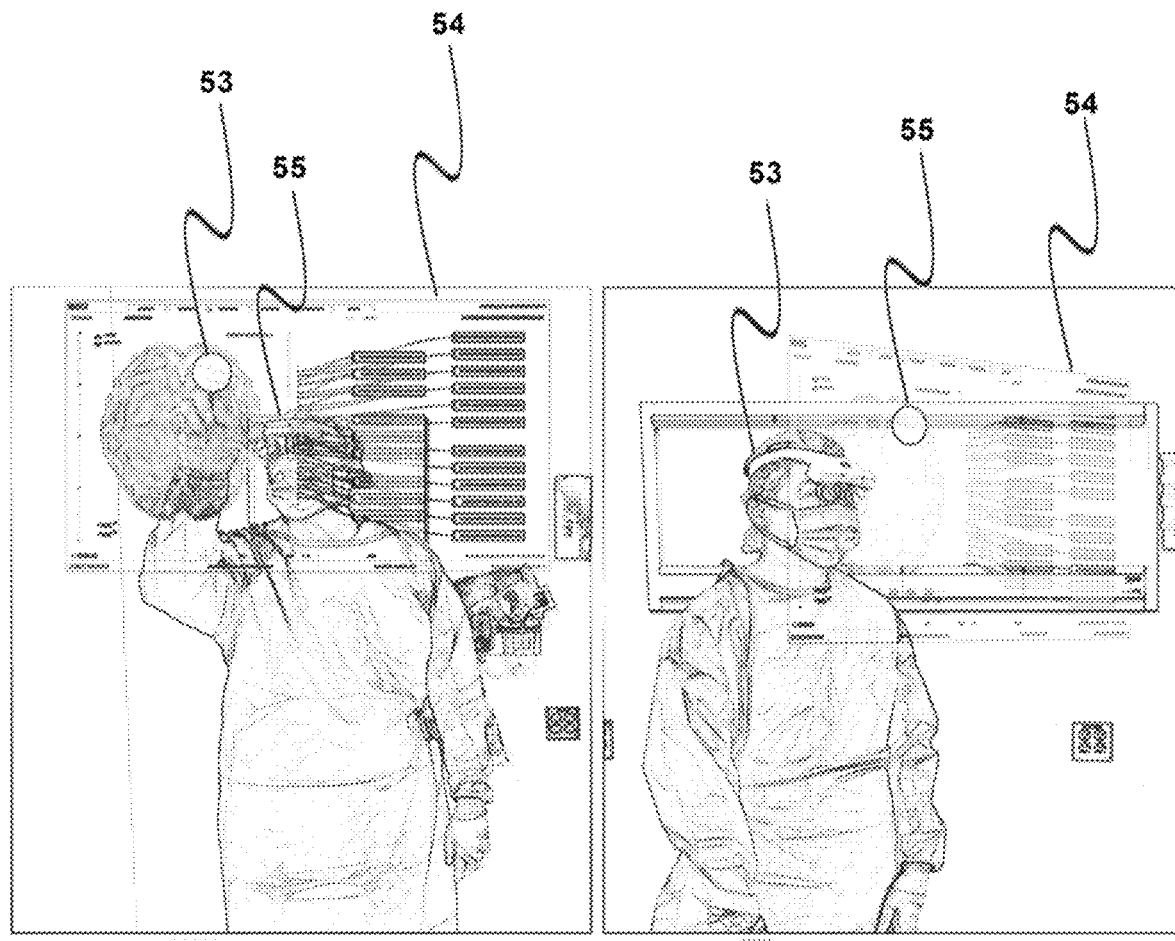
FIG. 10 is a diagrammatic illustration of the remote surgery assist feature with both surgeons seeing the same virtual information and area of interest.

As shown in FIG. 10, the AXR headset system may be in communication with one or more second systems such that one or more remote users 53 can view the same images 54 from the system on the one or more second systems and communicate will the user and other remote users and together focus on a common area of interest 55. In the preferred embodiment all participants would wear the same model AXR headset and be connected wired or wirelessly. However, while the field medic will likely be wearing the AXR headset, the resulting video and data transfers on the other end could be through any 3D display with command-and-control features.

The AXR headset can be worn at the surgery site or remotely providing multiple parties with a real-time experience of the surgery to all headset wearers. By utilizing gesturing recognition and other mentioned technologies embedded in all user's headsets, any number of wired or wireless connected, or networked users may see the same virtual image. Then, any connected user can point to a specific point or set of points, or define one or more areas in virtual space, on the commonly seen virtual image in all the user's AXR headsets, which may then communicate and correspond that same reference information into the view of a select set or all other user's AXR headsets or to any other monitors and displays in the network. In other words, for example, if using eye-tracking or head tracking, the field medic or specialists may move his or her head or eyes at a predetermined degree of rotation, for instance 15 or 30 degrees either to the side or up and down to see the transmitted and received overlayed information. With this turn of the eyes or head, the video feed images may disappear and alternative information like patient vitals may appear. When the user moved his or her head or eyes the opposite way, other information such as patient vitals may appear.

To accomplish this forward assistance telemedicine, the AXR headset may include a 3G, 4G, or any other radio signal modem. In addition, a 5G modem to be capable of edge computing at multi-gigabit speeds. 5G multi-access edge computing (MEC) may be located on the battlefield which is a technique to migrate computing and traffic from a centralized cloud to the edge of a network, such as a localized mini datacenter close to the battlefield where all computing is restricted to just the towers placed on and around the battlefield or other geolocated data center near the physical battlefield location. In this fashion, data is collected and processed near the battlefield location and none of the voice or data traffic can go beyond the battlefield cell towers, to for instance an existing city cellular system, thus keeping voice and data traffic more secure, while reducing latency and providing real-time performance for high bandwidth applications. The 5G controller, managed behind the fighting line, can also permit voice and data traffic out to the larger (metropolitan) network, if there is a need, but otherwise keeps it restricted to just the towers and antennas which comprise the closed 5G MEC system.

Alternatively, the wireless software connection within the AXR headset system may leverage existing wired/wireless networking infrastructure to achieve connectivity where no battlefield restricted MEC system exist. The AXR headset system may be connected with some or all its components and sighting subsystem via a satellite, wireless or a technology such as Bluetooth®. The 5G MEC system so that the system may support multiple talk and data activities for multiple warfighters and where reliability is increased, the throughput supports massive data transfers, latency is reduced, and throughput of data is increased to a projected 100 Mbps with potentially greater than 10 Gbps peak speeds. Latency is a time interval between the input to a simulation and the visual or auditory response to this input. The AXR headset system may have more than one modems for redundancy, including the potential for a wired connection between the headset and the sighting subsystem.

The system may utilize a high-resolution high-speed wireless video connection from the outside sources, such as command or intelligence sources with the AXR headset's antennae as shown in FIG. 3, being connected together with a 5G multi-access control (MEC) system, which has antennas located within a battlefield, bivouac, or other camp location with the database also inside the perimeter of the 3G, 4G, 5G, or other wireless antennas.

In the instance of 5G MEC, which is a closed system which does not permit the transfer, computing and analysis end of the voice or data chain to go outside of the internally controlled system (battlefield or other specified location) a medic can wear a connected AXR headset and permit a video transfers from and to a reward battlefield surgery hospital at a remote location to see the action wounds and injuries of a warfighter and be able to gain assistance from the rearward healthcare professionals on treating such wound and injuries in real-time thus it can provide throughput rates with zero latency. This is compared to a typical wireless internet or cell system which may have 60-90 or more milliseconds or up to a minute delay and would typically have trouble with reliable downloads of compressed imagery.

The headset may include two 4K embedded cameras for field operations, together with simultaneous localization and mapping technology, hand-gesturing, finger-gesturing, and eye-tracking to help the remote and on-site surgeon communicate areas of concern or interest. Thus, assisting experts like surgeons may assist in performing surgery from a physically distant location or request an assist from another subspecialist who would also have the appropriate visualization from the field medic.

The AXR headset system controller and software may run as a bidirectional communication between a host/server and a client to transfer voice data, images, and telemetry information between the two devices (virtual or physical) for display on any of the viewports. The AXR headset system controller and software may handle remote inputs, which are sent back to the server and evaluated or executed. This may enable high-performance computing to be processed by a powerful machine remotely through the cloud or on a localized network. This methodology may work on wired, satellite, wireless, and cellular networks such as 5G. The AXR headset system may permit multiple warfighters to connect to one AXR headset to enable a multi-warfighter to see the same information one warfighter sees as an interactive broadcast experience, such as in a tank moving in a certain direction, so all AXR headset wearers can see and evaluate the same information. The AXR headset system may connect any of the components, equipment, or bio-information (like vital signs, exhaustion, etc.) of a warfighter, or all of them to another system such that the warfighter may be remotely monitored or sent to a senior officer on or off the battlefield.

The AXR headset system software may enable other connected warfighters or superiors or specialists to efficiently render the incoming frames using a variety of coding libraries, such as OpenGL or Metal. The AXR headset system may support Windows, macOS, x86-64 Linux, Android, IOS, and chromeOS and can be adapted to work with future operating systems. The AXR headset system software may support up to or more than 6k video at 120 frames per second and in the future may have increased resolution and frame rates. Frame rate is expressed in frames per second (FPS) which is the frequency rate at which consecutive images called frames appear on a display. Increasing the frame rate of video divides this sequence of images into smaller periods of time, which is another method to reduce the latency and improve system performance, which is beneficial in a surgery visualization situation.

Wireless communication from the headset to any peripheral component, like the sighting system or external system, like another warfighter with an AXR headset system may also be accomplished through optical communication or through any satellite or radio-frequency (RF). RF requires a transmitter and a receiver or a transceiver that incorporates both. RF communications may be used over a proprietary or a predefined protocol such as Zigbee, Bluetooth, Bluetooth Low Energy, Z-wave, or Wi-Fi. In this instance, a transmitter module is an electronic sub-assembly that is capable of transmitting a radio wave and modulating that wave to carry data. A receiver module is also an electronic sub-assembly that receives a modulated RF signal and demodulates it.

The wireless technology may also employ video over IP, also called streaming, using existing standards or proprietary methods for encoding the material into a bitstream, and then using an internet protocol (IP) network to carry that bitstream encapsulated in a stream of IP packets. A bitstream is a sequence of bits. A bit is a basic unit of information in computing. A bit represents a logical state of two possible values, which are most commonly represented as a "1" or "0" or binary digit. Because of the sequential nature of the video signal, resending packets is not an option. Additional error correction information may be added to the data transmission to ensure the stream can be reconstructed even if a few packets are lost in the transfer. The user may additionally or alternately wirelessly receive a 3D video feed from a digital microscope with wireless output, into the AXR headset, providing the surgeon with an alternative surgical video input.

The Eye-Tracking Subsystem.

The eye-tracking and subsystem 4 of the AXR headset may work through hardware and software. The head-tracking may work similarly. The software may be connected to the system's GPU working in connection with the system's modular controller. The eye-tracking may be captured by infrared light being projected into the warfighter's eye, which may create a glint or reflection, which may then be captured by one or more IR sensitive cameras 8. The eye-tracking subsystem 4 may be capable of capturing the glint from the eye from 30 frames per second to 500 frames per second. This information may be stored in real-time in the CPU and DSP, and then processed into a virtual space represented by x,y,z, or Cartesian coordinates. These coordinates may provide the system with the information about where the warfighter's gaze is in relation to the reflective lens and the alpha matte layer so that both stay aligned with the warfighter's gaze to provide a better virtual image on the AXR display. The eye-tracking subsystem may be used to map the warfighter's eye gaze and adjust not only the reflected images or video but also the alpha matte image located on the separate plane to keep the alpha combined image aligned with the eye box. Thus, the eye-gaze and the alpha matte layer may be controlled by the eye-tracking subsystem 4 to always stay in sync.

In addition, eye-tracking may be used as an operator command option, where a warfighter would look or gaze at a virtual menu projected in 3D viewports and be able to select one or more options by staring or blinking one's eye while gazing at the menu.

The AXR Digital Target Acquisition System (DTAS)

Figure 1B:
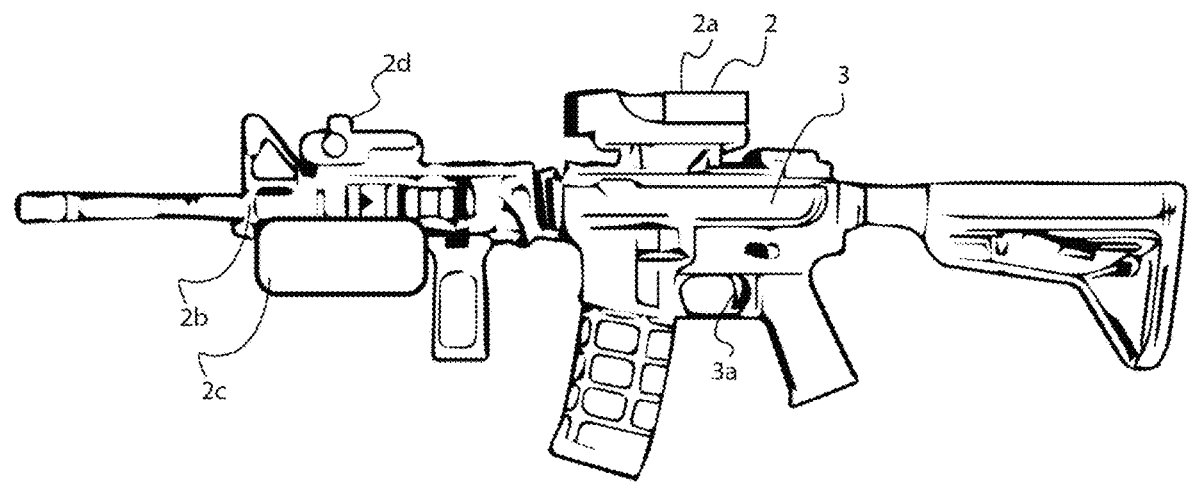
FIG. 1(b) is a diagrammatic illustration of a rifle with the digital target acquisition system enhancements.

As shown in FIGS. 1 and 1b, the AXR headset may have both front facing 5 and rear facing cameras 1a. The rear facing one or more cameras may use technology like SLAM and object identification to alert a warfighter of an oncoming activity or peril and alert the warfighter with an alert on the headset display screen or by an audible alert or other mechanism set out herein.

The AXR headset 1 described herein may be the same headset described in U.S. Pat. Nos. 9,955,862, 10,111,583, 10,874,297, U.S. patent application Ser. No. 17/137,069, U.S. patent application Ser. No. 17/137,093, U.S. patent application Ser. No. 17/151,174, U.S. patent application Ser. No. 15/962,661, U.S. patent application Ser. No. 16/511,202, U.S. patent application Ser. No. 16/511,451. U.S. patent application Ser. No. 17/034,944, and U.S. patent application Ser. No. 17/182,022, all of which are incorporated herein by reference.

The DTAS system combined with the features of the AXR headset system may provide enhanced targeting and alerting capabilities, including: (i) target capture via forward facing camera(s), (ii) target capture via weapons mounted camera(s), (iii) target capture through coordinated weapon and AXR headset coordination acquisition; (iv) rear facing threat alert camera, (v) checksum range finders through triangulation, (vi) threat alerts from all sensors and cameras, and (vi) target vs. hit/miss post-fire recording, analysis, and assessments for success displayed in the following fire feedback loop. The DTAS system may also use via AI to estimate for windage, distance, obstacles for instant corrective sight calibration. The see-through nature of the AXR lenses may provide for front see-through and peripheral vision for situational awareness and better heads-up ergonomics for weapons uses and battlefield awareness.

The DTAS may include forward facing camera(s), dual IMUs for higher accuracy of the system, wireless bidirectional connectivity from weapon to headset, laser range finder hardware and software in the DTAS system housing 2, and the potential for an automatic or remote firing actuator 3a to better help the warfighter attain a fire target, containing the target in the aiming mechanism, and fire with higher accuracy. The AXR headset system may comprise a virtual reality target acquisition and visualization system of the present invention, which may connect with a physically mounted sight 2 existing on the weapon 3. This AXR sight may be an existing weapon sight with an additional camera/digital module added or a totally new sighting module of digital nature to send target information to the AXR headset 1.

The sighting system 2 may have connectivity to the AXR headset 1 either by wire or wireless means. The sighting system 2 may also have optical zoom as well as digital zoom. The optical zoom may be in the camera and sensor subsystem, which may also have digital zoom, and the remaining digital zoom may be in the virtual display system and controller of the AXR headset system. The zoom mode may be controlled remotely from the headset 1 by voice command, gesturing technologies, eye-tracking, or any of the other controlling technologies mentioned herein, including a manual slide or toggle button. Alternatively, the zoom mode may depend on a target acquisition, and then the controller would make the zoom automatically increase or decrease to keep the target, as it advances or retreats in the same zoom view. This configuration may allow better heads-up situational awareness and continual monitoring of the target acquired.

Sensors in the AXR headset system may monitor with its on-board sensors or receive external information to be logged in and analyzed by the controller about such real-time trajectory factors, including the target's distance, wind, elevation, obstacles, and type of munition. The AXR headset system processing, machine learning, and AI may account for these factors in identifying the exact marked time to fire the weapon.

Computer vision (CV) artificial intelligence (AI) software enhancements could also be used to identify visual elements at which the munitions should intersect. AI could also be used as mentioned above to help identify the precise timing of munition release for target acquisition.

The augmented reality headset may display a distant target in two ways, firstly through the headset mounted camera and secondly via a wirelessly connected camera mounted on a weapon targeting sight. These two separate systems may be visually overlaid in the headset view. Using the headset mounted camera/heads up display (HUD), the user may select a target via a headset user interface, i.e., eye tracking menu selection. Once the target is selected, the video feed from the weapons sighting camera may be overlaid and when the weapons sighting crosshairs intersect the selected target, a signal may be sent to fire the weapon. Based on the calibration loop and direction and speed of movement of the weapon, the firing command may be given in advance of target acquisition by the estimated time delay to estimate target acquisition, including any inherent transmission delays. To enhance target acquisition, the controller and software enhancements and memory may also be used to mark points on the visual elements displayed in the AXR headset, in non-real time. After marking, the calculations provided by the AXR processing to the digital sight 2 may optimize the timing for munitions release at the time the marked image aligns with the munition's trajectory path when looking at the real-world target. The firing may be manually triggered upon a prompt from the system, or alternatively, the trigger may be pulled by an electromechanical device connect to the weapon trigger and activated only when in target acquisition mode when a target has been acquired by the warfighter.

By using a digital sighting system, the warfighter may also have the benefit of a feedback loop. The idea is that the warfighter has a recording loop while identifying and acquiring the target, but then the AXR headset processor and controller cause a continual monitoring of the munitions trajectory and hit location maybe using automatic zoom mode, if necessary, to identify where the munitions hit the target. If the target is hit and goes down, the system may reset for another shot, or if using this feedback loop, there could be digital corrections on the fly that could automatically correct for windage, range, etc.

The AXR headset and sight camera system may use laser, LIDAR, or other range finding mechanism or sensor. An inertial measurement unit (IMU) may be attached to the digital sight 2 and may be able to pre-determine the moment of when the firing should begin and keep tracking the target for continued fire correction. The system may record success rate, continuously learning and adapting. Additionally, windage and range information may be loaded on the front end to make the first shot have a higher success rate. The post-shot tracking may help further refine alignment for differences in predicted and actual windage and range information. The system may also comprise wireless bidirectional connectivity to the (i) weapon system(s), (ii) command, (iii) warfighting peers, (iv) drones, or (v) other needed connections. An inertial measurement unit (IMU) 2a may be attached to the digital sight 2 and may be able to pre-determine the moment of when the firing should begin and keep tracking the target for continued fire correction. The system may record success rate, continuously learning and adapting. Additionally, windage and range information may be loaded on the front end to make the first shot have a higher success rate. The post-shot tracking may help further refine alignment for differences in predicted and actual windage and range information.

Figure 11:
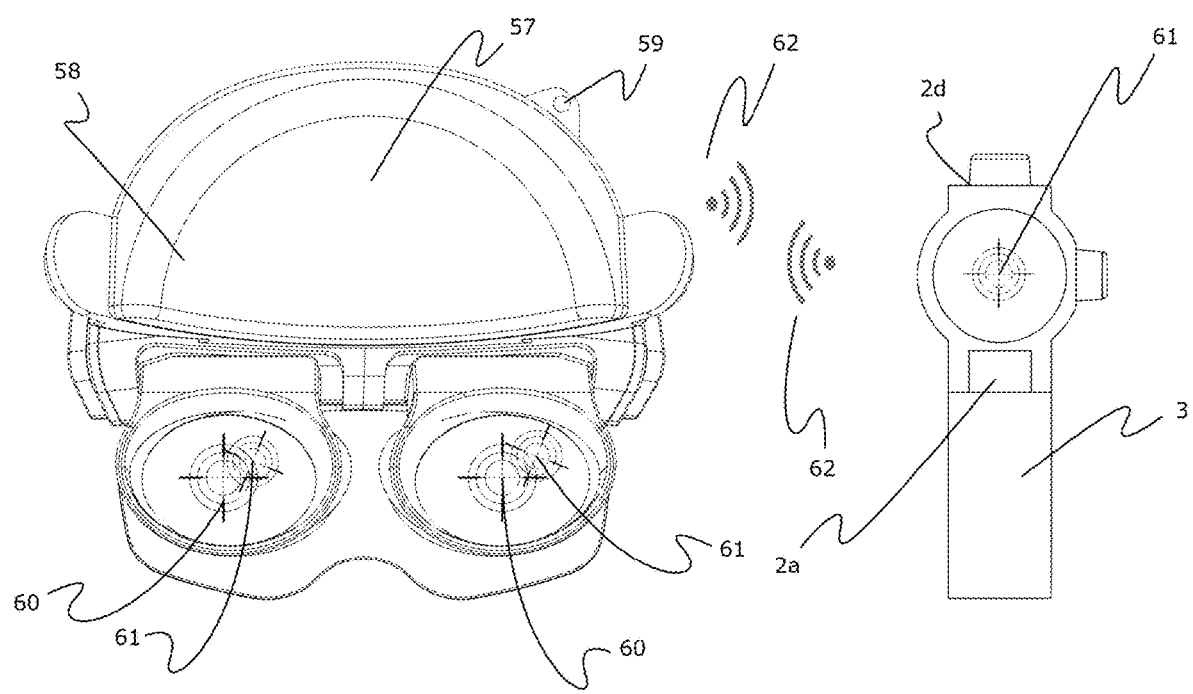
FIG. 11 is a AXR based digital target acquisition system with a sight mechanism and an augmented reality headset with wireless bidirectional connectivity.

As shown in FIG. 11, the AXR headset and DTAS system may employ the compute engine 57 in connection with the headset IMUs 58 and/or weapon 3 IMUs 2A, 2b with information from the range finder subsystem and sensors 59 which may display a distant target in two ways, firstly through the headset mounted display 60 and secondly via a DTAS derived crosshairs 61, which may be rotated 45 degrees. The DTAS targeting sight 2 and rangefinder 2d may be bidirectionally wirelessly connected 62 between the headset and the weapon system. These two disparate (one by 45-degree rotation) crosshairs symbols may automatically align in a visually overlaid configuration in the headset display. Upon center crosshair align indicate computed target acquisition for firing. If the target acquisition cannot be computed, the crosshair pairs will not align.

In another alternative, using the AXR headset mounted camera 5 the user may select a target via a headset user interface, i.e., eye tracking menu selection. Once the target is selected, the video feed from the weapons sighting camera may be overlaid and when the weapons sighting crosshairs intersect the selected target, a signal may be sent to fire the weapon. Based on the calibration loop and direction and speed of movement of the weapon, the firing command may be given in advance of target acquisition by the estimated time delay to estimate target acquisition, including any inherent transmission delays.

One or more IMUs 2b may be attached nearer the barrel of the weapon to provide a more accurate measurement of weapon barrel position. The system can combine the second IMU 2b with the IMU 2a mounted on the digital sight 2 as a means to compensate for the drift inherent in IMUs. Multiple IMUs in a known configuration, which may be aligned in all axes, or transversally aligned in one or more axes, can also compensated for cross axis sensitivity, scale factor errors, and aid in reducing repeatability errors.

Cross-axis sensitivity is defined as the parasitic measurement induced by solicitation along an axis orthogonal to sensor axis, thus a transaxially mounted IMU can compensate for this cross-axis sensitivity. This is useful information for the AR headset 1 to be able to augment the vision of the warfighter with an approximation of where the weapon is targeted.

Another improvement may be a stabilization system 2c attached to the weapon 3 and controlled by the CV and AI of the AR headset 1 to improve the stability of the weapon while aiming. This stabilization system can consist of a gyroscope of various constructions, Brushless DC motors combined with a gimbal mount for 3 axis stabilization in communication with IMU 2a and secondary IMU 2b. The stabilization system is a stock, or a typical holding point of the weapon while aiming. This stabilization system creates a buffer between the guiding hand and the actual weapon barrel to allow for stabilization. This will reduce the time of re-aiming as it is related to kickback. The stabilization system, in concert with the AR headset and AI algorithms, can bring the weapon back in line with the previous sight by actively adjusting the stabilization system by utilizing inputs from IMU sensors on the weapon, as well as information from the AR headset cameras and other sensors. Information displayed on the AR headset 1 may advise the warfighter when the weapon is back in alignment and ready to scan the target to be acquired. Real time eye-tracking may be embedded in the AR headset 1 to help the system determine the areas of interest.

Another improvement may be the inclusion of a range finder 2d. This range finder can utilize technologies including ToF sensors or LIDAR. This range data provides necessary information about distance to target, so that the digital sight 2 is able to be accurately modified for a more accurate deployment of munitions. This information, along with the digital sight output and the information received from the IMU sensor 2a and secondary IMU sensor 2b can be processed in the AR headset 1 to provide a real time mapping of the target object to be presented to the warfighter in the AR display.

In another embodiment of the invention, an accelerometer, gyroscope, and a magnetometer in the AXR headset or weapon may keep track of recoil measurements of the weapon as it fires and use this information in the calculation of target acquisition, The headset 1 may also be used for guided projectiles like from a bazooka, which require a laser indicator for point of impact. The AXR headset 1 may support and control a self-mounted laser pointer, or a laser pointer mounted on a drone, fixed installation, etc. anywhere in the world.

Situational awareness may be improved by having the warfighter see the target from the headset 1, where the warfighter may still have significant peripheral vision, and not having to squint into the sight 2, and enhancing peripheral vision using forward mounting cameras 5 as well as backward/upward mounted cameras 6 to provide audio or visual alerts for encroaching enemy combatants or threats. By switching control/firing system to an other-than-forward-facing weapon, the warfighter may also mitigate threats in other-than-forward-facing directions. With robotically controlled aiming weapons systems, this could enable one or more hands-free weapon capability.

Further, current telescopic sighting systems are analog optical systems that provide a target overlay on one of the optical modules. This becomes a problem when the warfighter of the munitions is off axis of the sight, which causes the warfighter of the firearm to miss their target. A digital system, which may employ a fixed digital imaging system attached to the optical system, may always have the target overlay on-axis.

A typical rifle scope is around six degrees field of vision (FOV). This FOV is fixed for that optical system. The present invention may employ large pixel count imaging sensors (4k, etc.) to capture this entire FOV, and then re-present the digital image to the warfighter in a much larger field of view through the AXR headset 1. This may allow a greater effective resolution to the warfighter with both the virtual information about the target and the real-world information displayed to the warfighter's eyes.

The transmission of this video to the warfighter may need to be as latency free as possible. Depending on target movement, the latency may need to be no greater than 20 ms from image acquisition to output of the display.

Any number of wireless methods may be employed to transmit this video digitally, such as Bluetooth, ad hoc WiFi, etc.). In typical digital transmission where the throughput does not equal the raw pixel data from the imager, compression is typically employed.

The sighting system may communicate the areas of interest in the scene and then transmit those specific areas over uncompressed, while using pixel binning to throw away unused resolution in the rest of the scene. Alternatively, the weapon 3 may connect to the AXR headset 1 through a cord or wired solution.

The devices and methods discussed herein are merely illustrative of specific manners in which to make and use this invention and are not to be interpreted as limiting in scope.

While the devices and methods have been described with a certain degree of particularity, it is to be noted that many modifications may be made in the details of the construction and the arrangement of the devices and components without departing from the spirit and scope of this disclosure. It is understood that the devices and methods are not limited to the embodiments set forth herein for purposes of exemplification.

Whereas, the devices and methods have been described in relation to the drawings and claims, it should be understood that other and further modifications, apart from those shown or suggested herein, may be made within the spirit and scope of this invention.

What is claimed is:

1. An AXR target acquisition and visualization system comprising:
    an AXR headset including:
    a headset support frame;
    an optical system including:
    an image generator;
    a partially transmissive curved mirror positioned in front of a viewer eye;
    a beam splitter positioned between the partially transmissive curved mirror and the viewer eye; and
    an optical image relay configured to conjugate a two-dimensional (2D) image formed from the image generator to a curved focal surface of the partially transmissive curved mirror and including a prism having a folding surface configured for folding the optical path for light generated by the image generator towards the beam splitter;
    one or more forward and/or backward and/or upward mounted cameras connected to the headset support frame; and
    a digital target acquisition system including a processor coupled in communication with the optical system and the cameras, where the digital target acquisition system is capable of identifying enemy combatants and alerting the wearer of the AXR headset; and
    a digital sight capable of being mounted on a weapon, the digital sight in communication with the AXR headset;
    wherein the digital target acquisition system receives images from the digital sight and displays the received images on the partially transmissive curved mirror of the AXR headset.

2. The system of claim 1 where the digital sight is an existing weapon sight with an additional digital camera added.

3. The system of claim 1 where the digital sight is a sighting module of a digital nature capable of sending target information to the AXR headset.

4. The system of claim 1 where the communication between the digital sight and the AXR headset is wired.

5. The system of claim 1 where the communication between the digital sight and the AXR headset is wireless.

6. The system of claim 1 where the digital sight has optical and/or digital zoom capabilities, and where the zoom capabilities of the digital sight are controlled by the AXR headset.

7. The system of claim 1 further comprising computer vision artificial intelligence software enhancements.

8. The system of claim 7 where the computer vision artificial intelligence software enhancements are capable of identifying visual elements at which munitions should intersect and identifying the precise timing of munition release.

9. The system of claim 1 further comprising recording capabilities such that the system is capable of recording a feedback loop while identifying and acquiring a target and identifying where munitions hit the target and using the feedback loop to produce digital corrections in real-time.

10. The system of claim 1 further comprising an inertial measurement unit attached to the digital sight, where the inertial measurement unit is capable of pre-determining the moment when firing should begin and tracking the target for continued fire correction, as well as recording success rate, continuously learning, and adapting.

11. The system of claim 1 further comprising a gyro system capable of being attached to the weapon, where the gyro system is controlled by the AXR headset to lessen the impact of kickback and bring the weapon back in line with a previous sight or the previous sight plus an adjustment radius.

12. The system of claim 1 further comprising real-time eye-tracking embedded in the AXR headset, such that the system is capable of determining an area of interest based on eye-tracking.

13. The system of claim 1 where the AXR headset has a latency of no greater than 20 ms from image acquisition to display output.

* * * * *